US010407376B2

(12) United States Patent
Crockatt et al.

(10) Patent No.: US 10,407,376 B2
(45) Date of Patent: Sep. 10, 2019

(54) METHOD TO PREPARE PHENOLICS FROM BIOMASS

(71) Applicant: Nederlandse Organisatie voor toegepast-natuurwetenschappelijk onderzoek TNO, 's-Gravenhage (NL)

(72) Inventors: Marc Crockatt, 's-Gravenhage (NL); Jan Harm Urbanus, 's-Gravenhage (NL); Paul Mathijs Konst, 's-Gravenhage (NL); Martijn Constantijn De Koning, 's-Gravenhage (NL)

(73) Assignee: Nederlandse Organisatie Voor Toegepast-Natuurwetenschappelijk Onderzoek TNO, 's-Gravenhage (NL)

( * ) Notice: Subject to any disclaimer, the term of this patent is extended or adjusted under 35 U.S.C. 154(b) by 0 days.

(21) Appl. No.: 15/544,172

(22) PCT Filed: Jan. 18, 2016

(86) PCT No.: PCT/NL2016/050039
§ 371 (c)(1),
(2) Date: Jul. 17, 2017

(87) PCT Pub. No.: WO2016/114668
PCT Pub. Date: Jul. 21, 2016

(65) Prior Publication Data
US 2017/0349529 A1 Dec. 7, 2017

(30) Foreign Application Priority Data
Jan. 16, 2015 (EP) ................................... 15151530

(51) Int. Cl.
| C07C 67/347 | (2006.01) |
| C07C 67/08 | (2006.01) |
| C07C 67/31 | (2006.01) |
| C07C 67/317 | (2006.01) |
| C07C 37/00 | (2006.01) |
| C07C 37/20 | (2006.01) |
| C07C 37/50 | (2006.01) |
| C07C 37/62 | (2006.01) |
| C07C 213/02 | (2006.01) |
| C07C 231/02 | (2006.01) |
| C07C 51/09 | (2006.01) |
| C07C 51/367 | (2006.01) |

(52) U.S. Cl.
CPC .......... *C07C 67/347* (2013.01); *C07C 37/002* (2013.01); *C07C 37/20* (2013.01); *C07C 37/50* (2013.01); *C07C 37/62* (2013.01); *C07C 51/09* (2013.01); *C07C 51/367* (2013.01); *C07C 67/08* (2013.01); *C07C 67/31* (2013.01); *C07C 67/317* (2013.01); *C07C 213/02* (2013.01); *C07C 231/02* (2013.01)

(58) Field of Classification Search
CPC ... C07C 67/347; C07C 231/02; C07C 37/002; C07C 51/09; C07C 51/367; C07C 213/02; C07C 215/76; C07C 235/46; C07C 235/60; C07C 37/20; C07C 37/50; C07C 37/62; C07C 39/04; C07C 39/07; C07C 39/11; C07C 39/20; C07C 39/24; C07C 63/06; C07C 65/03; C07C 65/10; C07C 67/08; C07C 67/31; C07C 67/317; C07C 69/517; C07C 69/78; C07C 69/84
See application file for complete search history.

(56) References Cited

U.S. PATENT DOCUMENTS

| 6,194,406 B1 * | 2/2001 | Kane ................... C07D 401/14 514/218 |
| 6,423,704 B2 * | 7/2002 | Maynard ............. C07D 401/14 514/218 |
| 6,878,700 B1 * | 4/2005 | Link ................... A61K 31/454 514/183 |

FOREIGN PATENT DOCUMENTS

WO    WO2007/146636    * 12/2007

OTHER PUBLICATIONS

White et al (Basic Energy Sciences Advisory Committee Subpanel Workshop Report, Opportunities for Catalysis in the 21st Century, 2002, pp. 1-47). (Year: 2002).*
Moreno et al. (An Efficient One-Pot Synthesis of Phenol Derivatives by Ring Opening and Rearrangement of Diels—Alder Cycloadducts of Substituted Furans Using Heterogeneous Catalysis and Microwave Irradiation, SYNLETT, No. 7, pp. 1259-1263, (Year: 2004).*
Aysu et al. (Biomass pyrolysis in a fixed-bed reactor: Effects of pyrolysis parameters on product yields and characterization of products, Energy 64 pp. 1002-1025, Published 2014) (Year: 2014).*
Dianqing (Synthesis and biological activity of carbamoyl substituted phenoxylalkylamine derivatives, Zhongguo Yaowu Huaxue Zazhi / Zhongguo Yaowu Huaxue Zazhi vol. 20 Issue: 3 p. 181-186 Publication Date: 2010) (Year: 2010).*
Dianqing translated 2010 16 pages (Year: 2010).*
Moreno, Andres et al., An Efficient One-Pot synthesis of Phenol derivatives by Ring Opening and Rearrangment of Diets—Alder Cycloadducts of Substituted Furans Using Heterogeneous Catalysis and Microwave Irradation, SYNLETT (2004) No. 7, pp. 1289-1263.
Simmie, John M. et al., "Harmonising Production, Properties and Environmental Consequences of Liquid Transport Fuels from Biomass--2,5-Dimethylfuran as a Case Study", Chemsuschem vol. 6, No. 1 (Dec. 17, 2012) pp. 36-41, XP055500351.
McCulloch, A. et al., "Influence of Lewis acids on the Diels—Alder reaction. II. Rearrangement of 1- and 1,4- substituted diethyl 7-oxabicyclo[2.2.1]2,5-heptadiene-2,3-dicarboxylate adducts to 4- and 4,6-substituted diethyl 3-hydroxyphthalates", Canadian Journal of Chemistry, 1969, 47(23): 4319-4326 doi: 10.1139/v69-716.

* cited by examiner

*Primary Examiner* — Yevgeny Valenrod
*Assistant Examiner* — Blaine G Doletski
(74) *Attorney, Agent, or Firm* — Verrill Dana LLP

(57) ABSTRACT

The present invention is directed to a method for preparing a final phenolic product from biomass comprising the steps of providing a furanic compound obtainable from biomass; reacting the furanic compound with a dienophile to obtain a phenolic compound; reacting the phenolic compound further to obtain the final phenolic product.

20 Claims, 3 Drawing Sheets

METHOD TO PREPARE PHENOLICS FROM BIOMASS

The invention relates to the preparation of aromatic compounds from biomass. In particular, the invention relates to a method to prepare phenolics by reacting furanics obtainable from biomass.

Worldwide, the demand for products containing aromatic compounds such as benzene, toluene and xylene increases by 5% per annum. Currently, these aromatic compounds are mostly isolated or derived from fossil feedstock such as crude oil, tar and coal. These feedstocks are becoming increasingly expensive due to the increasing use of shale gas on the short- and mid-term, and the depletion of resources on the longer term. Furthermore, there is a growing interest in renewable chemicals and the reduction of the $CO_2$ footprint of chemicals. As such, alternative sources for aromatic compounds are required.

The use of biomass for the production of aromatic compounds offers an alternative route to secure supply and bears the potential to provide cost-competitive technology. Moreover, biomass is renewable and reduces the $CO_2$ footprint of chemicals considerably. Finally, the introduction of biomass as resource can result in aromatic compounds with additional functionality compared to fossil feedstock, which can be exploited in novel applications.

Currently, production of aromatics from biomass is not commercialized, although several technologies are under development. Of these, technologies that employ conventional reforming principles are most advanced. Such techniques crack biomass catalytically into an oil that also contains several important base aromatics (benzene, toluene, xylene). In essence, biomass is deoxygenated and stripped from its functionality resulting in poor yields (<20%), which will likely lead to tight and highly dependable business cases. To increase the likelihood of a positive business case, technology is required that partially preserves the functionality that is contained in biomass.

Functionalized aromatic compounds of interest contain at least one oxygen atom that originates from biomass. Examples include acids and their ethers/anhydrides (e.g. benzoic acid, benzoates, phthalates, mellitic acids), phenolics (e.g. phenol, cresols, resorcinol, xylenols), ethers (e.g. anisole), and hydroxyacids (e.g. hydroxybenzoic acids, hydroxyphthalic acids). Interestingly, such aromatics require multiple reactions when produced from fossil feedstocks leading to elevated cost prices, while the preservation of oxygen will lead to increased yields from biomass, thus potentially providing cost-competitiveness processes.

It is generally accepted that to preserve functionality, biomass constituents need to be unraveled and treated individually. Bio-refinery concepts are being implemented to fractionate biomass, allowing for separated conversion paths. Typically, biomass that is suitable for aromatics production comprises one or more of the following components: oils, fats, lignin, carbohydrate polymers (e.g. starch, cellulose, hemicellulose, pectin, inulin), sucrose, sugar alcohols (e.g. erythritol).

Of these components, lignin already comprises aromatic compounds. Therefore, it is considered in the field to be the most promising biomass component from which aromatics, phenolics in particular, can be obtained. Phenolics are of great interest for the wide variety of applications, ranging from precursors for plastics and coatings, to pharmaceutical intermediates, to dyes, pesticides and ingredients in flavors & fragrances.

WO-A-2009/021733 discloses the hydrolysis of lignin to obtain phenolics. Harsh conditions such as strong acids and high temperatures are reported to be required and a complex mixture of a variety of phenolics are obtained.

US-A-2012/0302796 discloses the depolymerization of lignin catalyzed by heterogeneous solid acid catalyst and high temperatures of typically 215-300° C. A variety of phenols are found amongst the products.

US-A-2013/0150630 discloses the hydrogenation of pre-depolymerized lignin to obtain phenols from biomass.

Drawbacks of the conversion of the lignin component from biomass are the required harsh conditions, low yields and complex mixtures of products. These drawbacks result in costly processes which are, thus far, not commercially viable.

The inventors found that aromatic compounds can be prepared from carbohydrates, the largest constituent of most biomass, thereby circumventing the drawbacks found in the methods based on lignin. In order to prepare aromatic compounds from biomass, carbohydrates are first converted into one or more furanic compounds.

One or more of said furanic compounds is reacted with a dienophile to obtain an aromatic compound. So far, this technology has been geared toward base aromatic chemicals such as benzene, toluene and xylene, thereby eliminating completely the original functionality of biomass. As a consequence, the business case utilizing this technology equals the poor business case based on classical reforming techniques.

Surprisingly, the inventors found that phenolics, aromatic compounds with a higher (financial) value compared to base aromatics, can also be prepared by reacting furanic compounds with dienophiles. In order to obtain phenolics from biomass, carbohydrates are first converted into one or more furanic compounds. One or more of said furanic compounds is reacted with a dienophile to obtain a phenolic. Said phenolic is then reacted further to obtain a final phenolic product.

Thus the invention relates to a method to prepare phenolics from biomass comprising the steps of:
a) providing a furanic compound obtainable from components of biomass;
b) reacting the furanic compound with a dienophile to obtain a phenolic compound;
c) reacting the phenolic compound further to obtain a final phenolic product.

Figure 1:
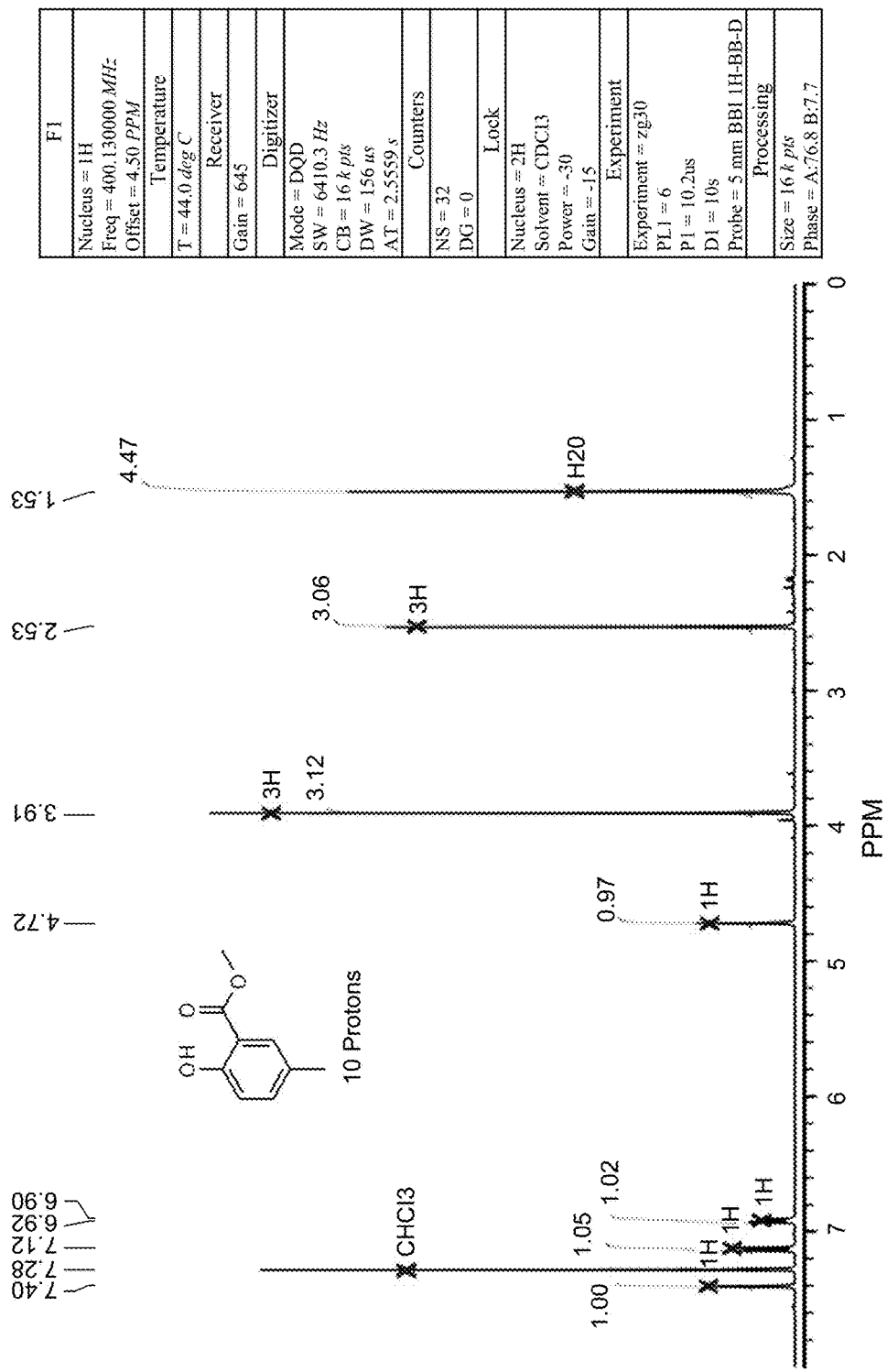
FIG. 1 is an NMR spectrum of methyl 2-methyl-5-hydroxy-benzoate which is a compound obtained in accordance with the present invention.

The reaction that combines a furanic compound and a dienophile to produce a phenolic compound, or aromatic compound in general, is a so-called Diels-Alder cycloaddition reaction. The Diels-Alder reaction of furanics is well documented for a variety of dienophiles. Alkenic dienophiles form the bulk of the literature. Furthermore, the Diels-Alder reaction of biomass derived furanics to base aromatics, such as benzene, toluene and xylenes, has been disclosed. Generally, said furanic is reacted with a lower alkene gas, such as ethene or propene, utilizing an appropriate catalyst and highly elevated temperature and pressure.

These aggressive conditions lead to the formation of significant levels of by-products.

WO2013040514 discloses the reaction of 2-methylfuran and 2,5-dimethylfuran (DMF) with ethylene gas, yielding toluene and p-xylene respectively, at temperatures of 175° C. and pressures of >53 bar.

WO2010151346 discloses the reaction DMF with ethylene to yield p-xylene, utilizing a carbon catalyst, temperatures of >330° C. and pressures>34 bar.

WO2009110402 discloses the reaction of DMF with ethylene, catalyzed by dichlorotitanocene, at 180° C. for 3 hours.

U.S. Pat. No. 2,405,267 discloses the Diels-Alder reaction between furan and ethylene yielding the bicyclic adduct 7-oxabicyclo[2.2.1]hept-2-ene. This process uses temperatures of 155° C. and pressures of 83 bar for 16 hours in 5-8% yield.

The extreme conditions combined with the catalysts in these reactions facilitate the Diels-Alder reaction and, often, an in situ ring-opening reaction.

When using more activated alkene dienophiles, and therefore milder processing conditions, a two-step process is normally utilized. WO2010012442 discloses the uncatalyzed Diels-Alder reaction of 2-ethylfuran with maleic anhydride, followed by ex situ ring-opening of the bicyclic adduct with sulfuric acid to yield 3-ethylphthalic anhydride and 3-ethylphthalic acid.

In situ ring-opening of bicyclic alkene based Diels-Alder adducts is also reported. Synlett, (6), 753-756; 2001 discloses the reaction of 2-ethylfuran with maleimide to yield 3-ethyl-N-methylphthalimide in one step when utilizing Lewis acid catalysts supported on silica.

Said references of reactions of furanics with alkenic dienophiles disclose technologies to produce non-phenolic bulk compounds, such as benzene, toluene and xylene. The present invention is directed to phenolic compounds.

Reaction of furanics with alkynes are reported to yield medium- to highly-functionalized phenolics (tri-substituted or greater). Said publications exclusively utilize activated dienophiles and, optionally, Lewis acid catalysis, to facilitate mild processing conditions. Examples of said dienophiles are methyl propiolate, dimethyl acetylenedicarboxylate (DMAD), benzynes, and 1,1,1,4,4,4-hexafluoro-2-butyne. The use of a catalyst generally yields the phenolic directly via an in situ ring-opening process, whereas processes which exclude a catalyst generally yield a bicyclic intermediate which must be ring-opened to the phenolic ex situ.

WO2008071736 (Pharma), WO2009150118 (Pharma), WO2009150119 (Pharma), WO2009072581 (Pharma) disclose the reaction of 2-methylfuran with alkyl propiolates, under Lewis Acid catalysis, to yield the corresponding phenol, at atmospheric pressure and temperature. These processes yield 30-40% in under 1 hour. In all cases, the product of these reactions is further decorated to yield more chemically complex molecules for pharmaceuticals. The above-mentioned Pharma references all describe the use of the Diels-Alder product as an intermediate en route to significantly more chemically complex pharmaceutical molecules. In all cases, the relevant groups which are built in with this technology are retained in the final product. None of these are directed towards bulk aromatics.

The Diels-Alder reaction between furan-derivatives and DMAD is disclosed in WO2005042500 (Pharma), WO2008075955 (no bicyclic adduct opening—use of activated chemicals), CN101824108 (no bicyclic adduct opening—catalyst), WO2004002617 (no bicyclic adduct opening—directed to new temperature control device for microwaves), and WO2002053567. The processing conditions vary considerably, but are generally mild. In all but the first reference of this paragraph, the reaction is stopped at the bicyclic adduct, and bicyclic adduct opening reactions are not performed. Only the first describes the bicyclic adduct opening process to yield an aromatic, but this is an intermediate en route to significantly more chemically complex pharmaceutical molecules where the relevant groups which are built in with this technology are retained in the final product. Again, none of these are directed towards bulk aromatics.

WO2005123069 discloses the Diels-Alder reaction of furan with a benzyne to yield a bicyclic adduct product, followed by ex situ ring-opening of said bicyclic adduct product under protic acid conditions to yield the corresponding napthol. This chemistry is only relevant for the synthesis of napthols.

U.S. Pat. No. 6,878,700 discloses the Diels-Alder reaction of furan derivatives and 1,1,1,4,4,4-hexafluoro-2-butyne to yield the corresponding bicyclic adduct. Said bicyclic adduct is then ring-opened to the corresponding phenol under influence of a Lewis Acid catalyst. In this case, the ortho-di-trifluoromethyl aromatic is the specific target of the chemistry, and forms the basis of a much more complex pharmaceutical product.

Said references reporting reactions of furanics with alkynes to yield phenolic compounds were directed toward pharmaceutical molecules, either via the bicyclic adduct or the highly functionalized phenolic product. The present invention may be directed to the direct production of bulk phenolics which requires simple chemical conversion processes.

WO2013040514 discloses the high temperature, high pressure conversion of DMF and ethylene to p-xylene, via an in situ ring-opening of the bicyclic intermediate, followed by oxidation to the more desirable terephthalic acid.

Chemistry—A European Journal 17(44), 12452-12457, 2011 discloses the sub-ambient temperature, atmospheric pressure Diels-Alder reaction of DMF and acrolein to yield a bicyclic adduct. The aldehyde in said adduct is then oxidized to the carboxylic acid in situ, and the ring-opening performed ex situ by application of a protic acid. Said carboxylic acid is then removed by a decarboxylation process to yield p-xylene.

In the context of the present invention, the term C6-sugar refers to carbohydrate monomers comprising six carbon atoms and the term C5-sugar refers to carbohydrate monomers comprising five carbon atoms. For instance, carbohydrate polymers such as starch, cellulose and inulin comprise C6-sugar units such as glucose and fructose. The carbohydrate polymers hemicellulose and pectin comprise for instance C5-sugar units such as xylose and arabinose and C6-sugar units such as rhamnose and galactose. Sucrose is a dimer of the C6-sugar units glucose and fructose.

The conversion of e.g. starch, cellulose and hemicellulose into furanics can be effected in a one or a two-step procedure.

In a two-step procedure biomass is typically first pretreated to hydrolyze the cellulose and hemicellulose in order to obtain free sugars, i.e. non-polymerized sugars. This hydrolysis can be effected by means of enzymatic fermentation, acid catalysis, and the like. Said sugars are then converted in a separate step into one or more furanics by means of acid-catalyzed dehydrations.

In a one-step procedure, as is for instance disclosed in WO-A-2012/170520, the cellulose and hemicellulose are directly converted into one or more furanics by acid-catalysis.

U.S. Pat. No. 7,019,155 discloses the formation of furan from sugar alcohol such as erythritol, which may be considered as a type of C4-sugar.

WO-A-2007/146636 discloses the dehydration of sugars, e.g. fructose, to yield furan derivatives such as furfural and 5-hydroxymethylfurfural.

In the present invention, the furanic compound is reacted with a dienophile to obtain a phenolic compound. Such a reaction proceeds typically according to the following general reaction scheme:

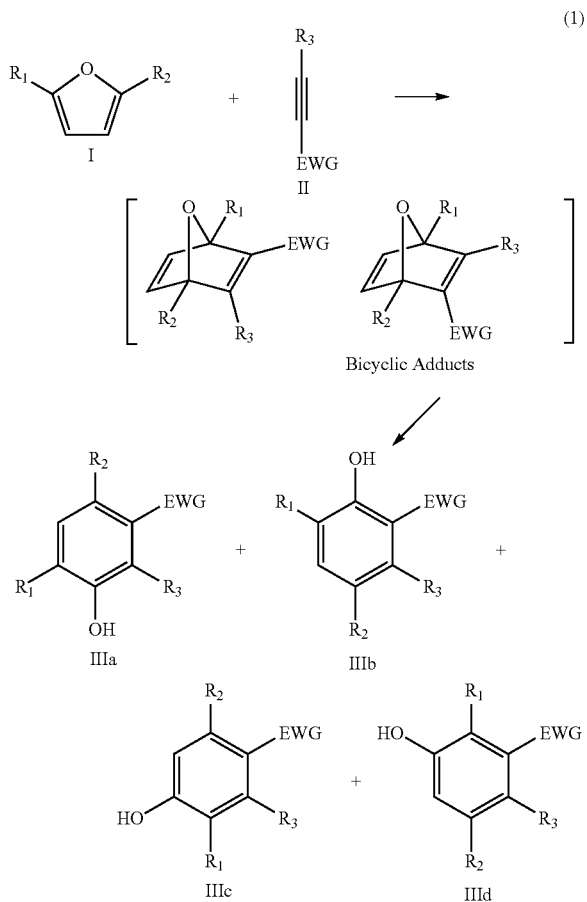

wherein the furanic compound is represented by formula I, the dienophile is represented by formula II and the phenolic compound is represented by IIIa, IIIb, IIIc or IIId or a mixture thereof.

Without wishing to be bound by theory, the inventors believe that the phenolic compound is formed via a bicyclic adduct that is formed as an intermediate.

Typically, the bicyclic adduct undergoes a ring-opening in situ. However, in a particular embodiment of the present invention, the phenolic compound is obtained by ex-situ ring-opening of a bicyclic adduct that is obtained after reacting the furanic compound with the dienophile.

In the present invention, the furanic compound may be considered as a diene. A reaction between a diene and a dienophile is known in the field as a Diels-Alder reaction. As such, for the present invention the reaction of the furanic compound with the dienophile may be referred to as the Diels-Alder reaction. However, it will be appreciated that the present invention is directed to any reaction of the furanic compound with a dienophile, independently of the specific reaction pathway of mechanism involved. For instance, although the Diels-Alder reaction is a concerted reaction, viz. a single-step reaction without any intermediate, a non-concerted reaction such as e.g. a Friedel-Craft-type pathway is also within the scope of the present invention.

In the present invention, the furanic compound obtainable from biomass may be provided as such, or as a precursor thereof. Such precursors are generally well known in the field. For instance, hexane-2,5-dione can be in situ converted into furanics. It may be appreciated that any method, way or procedure for providing the furanic compound obtainable from biomass is within the scope of the present invention.

The present invention is directed to provide a more environmentally benign method for the production of phenolic compounds. As such, it is preferred that the furanic compound is obtained from biomass. It may be appreciated that this is to be understood that the furanic compound is preferably truly obtained from biomass and not obtained from e.g. fossil fuel. The furanic compound is thus preferably obtained, and not merely obtainable from biomass as this has many advantages for the environmental impact of phenolic compounds preparation processes.

Given the limited variety of sugar units in biomass, only a limited variety of furanics are obtained directly from biomass. Therefore, in the present invention the variety of furanics is also limited. Typically, 2-(hydromethyl)furfural (HMF) is obtained from cellulose and furfural is obtained from hemicellulose. Both these compounds are relatively unstable and are thus typically converted to a variety of more stable furanics.

Hence, in the present invention, a furanic compound is based on the formula

typically substituted on the 2, 3, 4 and/or 5 position by one or more alkyl chains, heteroatoms and/or halogens. Said alkyl chains are typically $C_1$-$C_8$-alkyls and can be linear or branched and can be optionally substituted by halogens and/or heteroatoms. The furanic compound may be bound to a solid support so that purification after a reaction may be facilitated.

In a particular embodiment of the present invention, the furanic compound is substituted on the 2 and/or 5 position. Preferably the furanic compound is selected from the group according to formula I

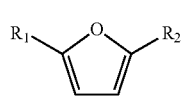

wherein $R_1$ and $R_2$ are heteroatoms, halogens or linear or branched $C_1$-$C_8$-alkyls, optionally substituted by halogens and/or heteroatoms. More preferably, $R_1$ and $R_2$ are independently selected from the group consisting of H, Me, F, Cl, Br, I, —CHO, —CH₂F, —CH₂Cl, —CH₂Br, —CH₂I, —CN, —NO₂, —CH₂NH₂ and amides thereof, —CH₂OH and esters or ethers thereof and —CO₂H and esters thereof. The furanic compound is optionally bound to a solid support, such as a resin, or the like.

The furanic compound may in particular be one or more compounds selected from the group consisting of the following compounds:

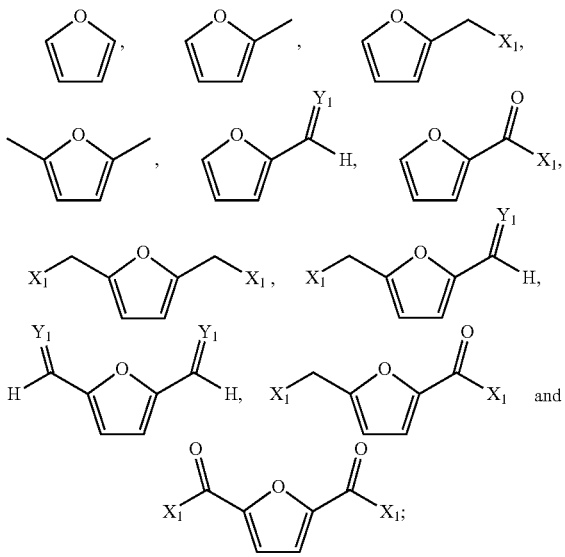

wherein $X_1$ is independently $OX_A$, $NX_AX_B$ or halogen, $Y_1$ is independently O, $NX_A$, N—$NX_AX_B$, N—$OX_A$ and $X_A$ and $X_B$ are independently hydrogen or hydrocarbon. This group of furanic compounds is particularly preferred since it consists of compounds that can readily be prepared from biomass.

In the present invention, the dienophile comprises a triple bond. The inventors found that for the present invention preferably an acetylene derivative according to the following formula II is used as the dienophile.

wherein EWG is an electron withdrawing group and $R_3$=H, linear or branched $C_1$-$C_8$-alkyl, or EWG. More preferably EWG=—CN, —NO₂, —CO₂X, —C(O)NX, —C(=NY)X, CF₃, CCl₃, CBr₃, Cl₃, —SO₂X, —SO₃X, —COH, —COX, —COF, —COCl, —COBr, —COI, wherein X and Y are independently H, or linear or branched $C_1$-$C_8$-alkyl, optionally substituted with halogens and optionally polymer-supported.

The dienophile may in particular be one or more compounds selected from the group consisting of the following compounds:

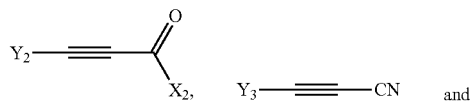

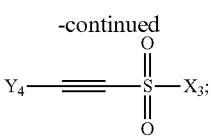

wherein $X_2$=H, $CH_3$, halogen, $OX_A$ or $NX_AX_B$; $Y_2$=H, $CH_3$ or $CO_2X_A$, $Y_3$=H or $CH_3$, $X_3$=$CH_3$, $OX_A$, $NX_AX_B$ or halogen, $Y_4$=H, $CH_3$, $SO_2X_3$; and $X_A$ and $X_B$ are independently hydrogen or hydrocarbon.

Acetylene derivatives according to formula II are easily obtainable from acetylene by a reaction of acetylene with e.g. $CO_2$ followed by further basic manipulations. These acetylene derivatives according to formula II are typically commercially available.

The dienophiles according to formula II react particularly well with the furanics of the present invention. The electron withdrawing group EWG results in an electron poor triple bond which reacts more rapidly with an electron rich furanic.

Additionally, the use of an acetylene derivative of formula II is preferable over the use of acetylene because acetylene poses significant safety hazards and subsequently requires extensive safety measures when worked with. In a particular embodiment of the present invention, the Diels-Alder reaction is catalyzed. Preferably the catalyst is a protic or a Lewis acid, optionally supported on a polymer a heterogeneous support such as silica. More preferably the catalyst is a Lewis acid based on a metal, preferably a metal selected from the group consisting of Zn, Al, Sc, B, Fe, Ir, In, Hf, Sn, Ti, Yb, Sm, Cr, Co, Ni, Pb, Cu, Ag, Au, Tl, Hg, Pd, Cd, Pt, Rh, Ru, La, Ce, Pr, Nd, Pm, Eu, Gd, Tb, Dy, Ho, Er, Tm, Lu, V, Mn, Y, Zr, Nb, Mo, Ta, W, Re, Os and combinations thereof. Even more preferably, the catalyst is selected from the group consisting of $ZnI_2$, $ZnBr_2$, $ZnCl_2$, $Zn(Ac)_2$, $Sc(OSO_2CF_3)_3$, $Y(OSO_2CF_3)_3$, $AlCl_3$, $Al(Et)_2Cl$, $BCl_3$, $BF_3$, $B(Ac)_3$, $FeCl_3$, $FeBr_3$, $FeCl_2$, $Fe(Ac)_2$, $IrCl_3$, $HfCl_4$, $SnCl_4$, $TiCl_4$ clays, zeolites and combinations thereof. Most preferably, the catalyst is selected from the group consisting of $ZnI_2$, $ZnBr_2$, $ZnCl_2$, $Sc(OSO_2CF_3)_3$, $Y(OSO_2CF_3)_3$, $AlCl_3$, $Al(Et)_2Cl$, $TiCl_4$ and combinations thereof.

The Diels-Alder reaction can be performed at a temperature ranging from −60-350° C., preferably −20-250° C., more preferably 20-150° C. The precise temperature depends on the specific furanic compound and dienophile used.

The Diels-Alder reaction may be performed by a pressure ranging from 0-200 bar, preferably 1-50 bar.

The Diels-Alder reaction is typically performed in a suitable solvent, preferably in a concentration of 0.1-3 M, more preferably about 2 M, selected from the group consisting of water, alcohols, esters, ketones, aliphatic hydrocarbons, aromatic hydrocarbons, organic acids, ethers, diprotic apolar solvents, halogenated solvents, nitrated solvents, ionic liquids, organic bases and combinations thereof.

Typical phenolic compounds that result from the Diels-Alder reaction are phenols according to the formula

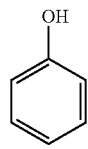

and are typically substituted on the 2, 3, 4, 5 and 6 position with one or more alkyl chains, heteroatoms and/or halogens.

Said alkyl chains are typically $C_1$-$C_8$-alkyls and can be linear or branched and can be optionally substituted by halogens and/or heteroatoms. In particular, the phenolic compound is a compound according to formulae

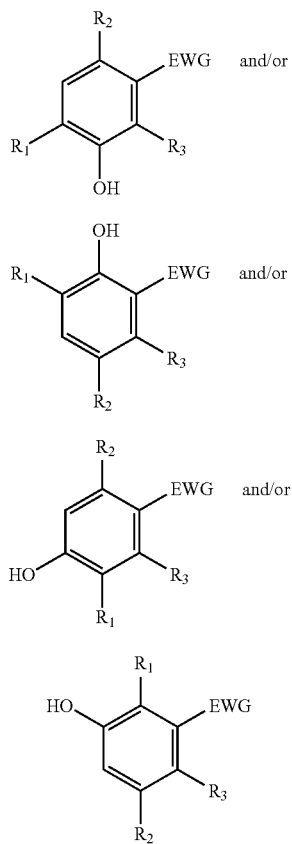

IIIa and/or

IIIb and/or

IIIc and/or

IIId wherein EWG is an electron withdrawing group and $R_1$, $R_2$ and $R_3$ are independently H, linear or branched $C_1$-$C_8$-alkyl, or EWG, more preferably $R_1$ and $R_2$ are independently selected from the group consisting of H, Me, F, Cl, Br, I, —$CH_2F$, —$CH_2Cl$, —$CH_2Br$, —$CH_2I$, —CN, —$NO_2$, —$CH_2NH_2$ and amides thereof, —$CH_2OH$ and esters or ethers thereof and —$CO_2H$ and esters thereof. More preferably EWG=—CN, —$NO_2$, —$CO_2X$, —C(O)NX, —C(=NY)X, $CF_3$, $CCl_3$, $CBr_3$, $CI_3$, —$SO_2X$, —$SO_3X$, —COH, —COX, —COF, —COCl, —COBr, —COI, wherein X and Y are independently H, or linear or branched $C_1$-$C_8$-alkyl, optionally substituted with halogens and optionally polymer-supported In a particular embodiment of the present invention, furanics derivable from C4-sugars are reacted in the Diels-Alder reaction. Typically, C4-sugars are converted into furan, i.e. the compound according formula I wherein $R_1$=$R_2$=H. Reactions with such furanics generally yield products according formula IIIa and IIIb or mixtures thereof, wherein $R_1$=$R_2$=H.

In another particular embodiment of the present invention, furanics derivable from C5-sugars are reacted in the Diels-Alder reaction with dienophiles. Typically, C5-sugars are converted into mono-substituted furanics, e.g. compounds according formula I wherein $R_1$=H and $R_2$ may be selected from the group consisting of Me, F, Cl, Br, I, —$CH_2F$, —$CH_2Cl$, —$CH_2Br$, —$CH_2I$, —$CH_2NH_2$ and amides thereof, —$CH_2OH$ and esters or ethers thereof. Reactions with such furanics generally yield products according formula IIIa and IIIb or mixtures thereof, wherein $R_1$=H.

In yet another particular embodiment of the present invention, furanics derivable from C6-sugars are reacted in the Diels-Alder reaction with dienophiles. Usually C6-sugars are converted into bis-substituted furanics, e.g. compounds according formula I wherein $R_1$ and $R_2$ are not hydrogen and may be independently selected from the group consisting of Me, F, Cl, Br, I, —$CH_2F$, —$CH_2Cl$, —$CH_2Br$, —$CH_2I$, —CN, —$NO_2$, —$CH_2NH_2$ and amides thereof, —$CH_2OH$ and esters or ethers thereof and —$CO_2H$ and esters thereof. Reactions with such furanics may yield products according formula IIIa, IIIb, IIIc and IIId or mixtures thereof.

The phenolic compounds such as IIIa IIIb, IIIc and IIId resulting from the Diels-Alder reaction are not necessarily desired final phenolic products. Therefore, preferably the phenolics compounds are further reacted in one or more reactions selected from the group consisting of hydrolysis, reduction, oxidation, decarboxylation, decarbonylation, nucleophilic addition, olefination, nitrosation, elimination, condensation, rearrangement, electrophilic substitution, and combinations thereof. In a particular embodiment of the present invention wherein the phenolic compound is a compound according to formula IIIa, IIIb, IIIc or IIId, this reaction generally involves conversion of $R_1$, $R_2$, $R_3$ or EWG or any combination thereof.

In the context of the present invention, said hydrolysis relates to the conversion of an ester to a carboxylic acid or alcohol, the conversion of an acyl halide to a carboxylic acid, the conversion of and amide to an acid, the conversion of an imine, hydrazone or oxime to a ketone, the conversion of a ketal or hemiketal to a ketone, the conversion of a halide to an alcohol, the conversion of a diazo-compound to an alcohol, the conversion of a nitrile to an acid or amide, the conversion of an ether to an alcohol.

Said reduction relates to the conversion of a carboxyl acid, an acyl halide or ester to an aldehyde, alcohol or hydrocarbon such as a methyl or another hydrocarbon, the conversion of a nitro to an amine, the conversion of a nitrile to an imine, aldehyde, or amine such as a methylene amine or another amine, the conversion of an aldehyde to an alcohol, hydrocarbon such as a methyl or another hydrocarbon or methylene amine, the conversion of a triple bond to a double bond or single bond, the conversion of a double bond to a single bond, and the conversion of a halogen to a hydrocarbon or a hydrogen, the conversion of an alkyne to an alkene, the conversion of an alkene to an alkane, the conversion of an amide to an aldehyde or an amine, the conversion of nitro to a oxime, a nitroso, a hydroxylamine, an amine/aniline, a hydrocarbon, a hydrazine compound, an azo compound, an azoxy compound, the conversion of an oxime to a hydroxylamine, the conversion of an azide to an amine and the conversion of a ketone or aldehyde with a amine to give an amine.

Said oxidation relates to the conversion of a hydrocarbon such as a methyl to an alcohol, an aldehyde or a carboxylic acid, the conversion of an alcohol to an aldehyde, a ketone or acid and the conversion of an aldehyde to an acid, the conversion of an alkene to an epoxide, the conversion of an amine to a nitro, a hydroxylamine, a nitroso or an amine to a N-oxide.

Said decarboxylation relates to the conversion of an carboxylic acid or carboxylate to a hydrocarbon or a hydrogen.

Said decarbonylation relates to the conversion of an aldehyde to a hydrogen or a hydrocarbon.

Said displacement reactions relate to the reaction of a halide with water to give an alcohol, with an alcohol to give an ether, with an amine to give an amine, with an thiol to give an thio-ether/thiol, with an acid to give an ester, with an azide to give an azide, with cyanide to give a nitrile, with a carbon nucleophile (hydrocarbon-lithiums, hydrocarbon-magnesium halides, hydrocarbon-zinc halides, alcohols, and the like) to give a hydrocarbon, the reaction of an activated alcohol (mesylate, tosylate, triflate and the like) with water to give an alcohol, with an alcohol to give an ether, with an amine to give an amine, with an thiol to give an thio-ether/thiol, with an acid to give an ester, with azide to give an azide, with cyanide to give a nitrile or with a carbon nucleophile (hydrocarbon-lithiums, hydrocarbon-magnesium halides, hydrocarbon-zinc halides, alcohols and the like) to give a hydrocarbon.

Said nucleophile addition relates to the conversion of an acid to a ketone or alcohol, the conversion of a nitrile to a ketone, imine or amine, the conversion of an aldehyde to an alcohol, the conversion of a halogen to another functionality, such as amine, alcohol, ether, alkyl, etc.

Said olefination relates to the conversion of an aldehyde or a ketone to an olefin such as styrene and the like.

Said nitrosation relates to the conversion of an amine to give a diazo-compound, an amine to give a halide or an amine to give an alcohol.

Said elimination relates to the conversion of a halide to give an alkene, an alcohol to give an alkene, an activated alcohol (mesylate, tosylate, triflate, etc.) to give an alkene or an amine/ammonium to give an alkene.

Said rearrangement relates to the conversion of an benzoic acid to a phenol or aniline, the conversion of an benzylic alcohol to a phenol, a Hoffman rearrangement, a Beckmann rearrangement or a Schmidt reaction/Curtius rearrangement.

Said electrophilic substitution relates to the electrophilic substitution of an aromatic hydrogen with an alkene to give an alkylbenzene, with a halide to give an aryl-halide, in a Friedel-Crafts acylation-type reaction to give a ketone, in a Friedel-Crafts alkylation-type reaction to give an alkylbenzene, in a nitration to give a nitrobenzene, in a Vilsmeier-type reaction/Gattermann-type reaction/Reimer-Tiemann-type reaction to yield a benzaldehyde, in a Kolbe-type process with $CO_2$ to give a benzoic acid.

Said condensation reaction relates to an aldol reaction and its variants, i.e. a reaction of the position a to an EWG (C(O)X, $NO_2$, CN, $SO_2X$, $SO_3X$, etc.) with an electrophile (Michael Acceptor, halides, hydrocarbon halides, activated alcohols, aldehydes, ketones, etc.), the reaction of an amine with an aldehyde/ketone to give an imine, an enamine, the reaction of an alcohol with an acid/ester to give a ester or the reaction of an amine with an acid/ester to give an amide.

Other reactions that may be carried out in the step of reacting the phenolic compound further to obtain the final phenolic product can be selected from the group of a reaction of a halide with a metal containing material (magnesium metal, zinc metal, methyl lithium, butyl lithium, etc.) to give a hydrocarbon-metal/hydrocarbon-metal halide/etc., the conversion of an acid to an amide, the conversion of an ester to an amide, the dehydration of an amide to a nitrile and the reaction of an activated alcohol (mesylate, tosylate, triflate, etc.) with a metal containing material (magnesium metal, zinc metal, methyl lithium, butyl lithium, etc.) to give a hydrocarbon-metal/hydrocarbon-metal halide and the like, an addition of a nucleophile (hydrocarbon-lithiums, hydrocarbon-magnesium halides, hydrocarbon-zinc halides, alcohols, etc.) to a nitrile to give and imine, an addition of a nucleophile (hydrocarbon-lithiums, hydrocarbon-magnesium halides, hydrocarbon-zinc halides, alcohols, etc.) to a nitrile to give a ketone, an addition of a nucleophile (hydrocarbon-lithiums, hydrocarbon-magnesium halides, hydrocarbon-zinc halides, alcohols, etc.) to a nitrile to give an amine, a Sandmeyer-type reaction of a diazo-compound to give a halide and a reaction of a halide or an activated alcohol in a metal catalysed cross-coupling reaction, such as Buchwald-Hartwig, Sonogashira, Heck, Suzuki, Stille, Negishi, Stille, Hiyama, and Kumada-type couplings.

According to the present invention, the step of reacting the phenolic compound further to obtain the final phenolic product may be achieved by chemical, bio-chemical, biological procedures or any combination thereof. Bio-chemical or biological procedures may typically involve fermentative, bio-catalytic or enzymatic conversions.

The inventors found that the phenolic compound is preferably further reacted in one or more suitable solvents, preferably in a concentration of between 3-10 volumes (kg solvent/kg starting material dissolved in it), in which the solvent may also be one or other of the reagents.

Furthermore, the inventors found that the reaction of the phenolic compound proceeds particularly well when catalyzed. Preferably a catalyst is a protic or Lewis acid or the like.

The final phenol product is phenol, or phenol substituted on one or more positions by alkyl chains, halogens and/or heteroatoms. Said alkyl chains are typically $C_1$-$C_8$-alkyls and can be linear or branched and can be optionally substituted by halogens and/or heteroatoms. Typically, the final phenol product is a compound according to formula

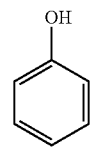

substituted on the 2, 3, 4, 5 and/or 6 position.

Preferably, the final phenol product is a bulk phenol, i.e. a phenol produced at bulk scale. A preferred final phenol product is therefore selected from the group consisting of phenol, o-alkylphenol, m-alkylphenol, p-alkylphenol, (e.g. cresols) o-hydroxybenzoic acid, m-hydroxybenzoic acid, p-hydroxybenzoic acid, 2,6-dialkylphenol, 2,5-dialkylphenol, 2,4-dialkylphenol, 2,3-dialkylphenol, 3,4-dialkylphenol, 3,5-dialkylphenol, (e.g. xylenols), 2,3,4-trialkylphenol, 2,3,5-trialkylphenol, 2,3,6-trialkylphenol, 2,4,5-trialkylphenol, 2,4,6-trialkylphenol, 3,4,5-trialkylphenol, o-nitrophenol, m-nitrophenol, p-nitrophenol, o-cyanophenol, m-cyanophenol, p-cyanophenol, catechol, resorcinol, hydroquione, o-halophenol, m-halophenol, p-halophenol, o-aminophenol, m-aminophenol. p-aminophenol, o-hydroxystyrene, m-hydroxystyrene, p-hydroxystyrene, o-hydroxybenzyl alcohol, m-hydroxybenzyl alcohol, p-hydroxybenzyl alcohol, o-hydroxybenzyl amine, m-hydroxybenzyl amine, p-hydroxybenzyl amine, o-hydroxyacetophenone, m-hydroxyacetophenone, p-hydroxyacetophenone, o-hydroxybenzaldehyde, m-hydroxybenzaldehyde, p-hydroxybenzaldehyde, o-hydroxybenzamide, m-hydroxybenzamide and p-hydroxybenzamide.

In a particular embodiment of the present invention, the final phenolic product is a compound according to following formulae IVa and/or IVa

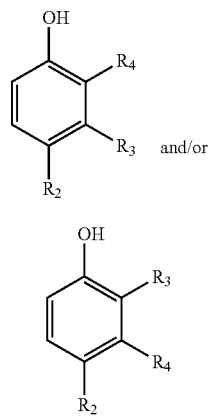

IVa

IVb wherein $R_2$=—H, linear or branched $C_1$-$C_8$-alkyl, —CH=CH$_2$, —CO$_2$X, —C(O)NX$_2$, —CH$_2$OX, —CH$_2$NX$_2$, —CHO, —OX, —CN, —NO$_2$, —C(O)NX, —C(=NY)X, —CF$_3$, —CCl$_3$, —CBr$_3$, —CI$_3$, —SO$_2$X, —SO$_3$X, —NX$_2$, —COX, —COF, —COCl, —COBr, or —COI, wherein X and Y are independently H, or linear or branched $C_1$-$C_8$-alkyl, optionally substituted with halogens and optionally polymer-supported; or and $R_3$=—H, linear or branched $C_1$-$C_8$-alkyl, —CH=CH$_2$, —CO$_2$X, —C(O)NX$_2$, —CH$_2$OX, —CH$_2$NX$_2$, —CHO, —OX, —CN, —NO$_2$, —C(O)NX, —C(=NY)X, —CF$_3$, —CCl$_3$, —CBr$_3$, —CI$_3$, —SO$_2$X, —SO$_3$X, —NX$_2$, —COX, —COF, —COCl, —COBr, or —COI, wherein X and Y are independently H, or linear or branched $C_1$-$C_8$-alkyl, optionally substituted with halogens and optionally polymer-supported; and $R_4$=—H, linear or branched $C_1$-$C_8$-alkyl, —CH=CH$_2$, —CO$_2$X, —C(O)NX$_2$, —CH$_2$OX, —CH$_2$NX$_2$, —CHO, —OX, —CN, —NO$_2$, —C(O)NX, —C(=NY)X, —CF$_3$, —CCl$_3$, —CBr$_3$, —CI$_3$, —SO$_2$X, —SO$_3$X, —NX$_2$, —COX, —COF, —COCl, —COBr, or —COI, wherein X and Y are independently H, or linear or branched $C_1$-$C_8$-alkyl, optionally substituted with halogens and optionally polymer-supported.

For instance, a compound IVb wherein $R_4$=Me or CH$_2$OH may be obtained from IIIa in a reduction reaction. A compound IVb wherein $R_4$=CO$_2$H may be obtained from IIIa in a hydrolysis reaction. Compound IVa wherein $R_4$=H may be obtained from IIIa in a decarboxylation or a hydrolysis and a subsequent decarboxylation reaction.

Preferably, the final phenolic product is a phenolic according to the formula IV, wherein $R_2$=Me and $R_3$=$R_4$=H, i.e. p-cresol.

In another preferred embodiment, the final phenolic product is a phenolic according to the formula IVa, wherein $R_3$=Me and $R_4$=$R_2$=H, i.e. m-cresol.

Thus, according to the present invention, p-cresol can e.g. be obtained from biomass by reacting 2-methylfuran (i.e. compound of formula I, wherein $R_1$=Me and $R_2$=H) with a propynoate (i.e. compound of formula II, wherein EWG CO$_2$X, and $R_3$=H), thereby obtaining specific phenolic compound of formula IIIa, wherein $R_1$=H, $R_2$=Me, EWG=CO$_2$X, and $R_3$=H. This specific phenolic compound is then subsequently reacted in a decarboxylation reaction or in a hydrolysis and a subsequent decarboxylation reaction to yield p-cresol.

In another preferred embodiment, the final phenolic product is a phenolic according to formula IV, wherein $R_4$=$R_2$=$R_3$=H, i.e. phenol.

According to the present invention, phenol can thus be obtained by reacting furan (i.e. compound of formula I, wherein $R_1$=$R_2$=H) with a propynoate (i.e. compound of formula II, wherein EWG=CO$_2$X and $R_3$=H), thereby obtaining a mixture of the phenolic compounds of formula IIIa and Mb, wherein $R_1$=$R_2$=$R_3$=H, EWG=CO$_2$X. This specific phenolic compound is then subsequently reacted in a decarboxylation reaction or in a hydrolysis and a subsequent decarboxylation reaction.

In another particular embodiment of the present invention, the final phenolic product is one or more phenolic selected from the group consisting of compounds according to the following formulae:

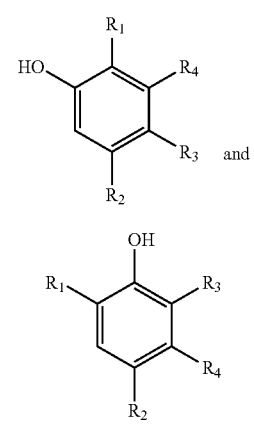

Va

Vb wherein $R_1$=linear or branched $C_1$-$C_8$-alkyl, —CH=CH$_2$, —CO$_2$X, —C(O)NX$_2$, —CH$_2$OX, —CH$_2$NX$_2$, —CHO, —OX, —CN, —NO$_2$, —C(O)NX, —C(=NY)X, —CF$_3$, —CCl$_3$, —CBr$_3$, —CI$_3$, —SO$_2$X, —SO$_3$X, —NX$_2$, —COX, —COF, —COCl, —COBr, or —COI, wherein X and Y are independently H, or linear or branched $C_1$-$C_8$-alkyl, optionally substituted with halogens and optionally polymer-supported; and $R_2$=—H, linear or branched $C_1$-$C_8$-alkyl, —CH=CH$_2$, —CO$_2$X, —C(O)NX$_2$, —CH$_2$OX, —CH$_2$NX$_2$, —CHO, —OX, —CN, —NO$_2$, —C(O)NX, —C(=NY)X, —CF$_3$, —CCl$_3$, —CBr$_3$, —CI$_3$, —SO$_2$X, —SO$_3$X, —NX$_2$, —COX, —COF, —COCl, —COBr, or —COI, wherein X and Y are independently H, or linear or branched $C_1$-$C_8$-alkyl, optionally substituted with halogens and optionally polymer-supported; and $R_3$=—H, linear or branched $C_1$-$C_8$-alkyl, —CH=CH$_2$, —CO$_2$X, —C(O)NX$_2$, —CH$_2$OX, —CH$_2$NX$_2$, —CHO, —OX, —CN, —NO$_2$, —C(O)NX, —C(=NY)X, —CF$_3$, —CCl$_3$, —CBr$_3$, —CI$_3$, —SO$_2$X, —SO$_3$X, —NX$_2$, —COX, —COF, —COCl, —COBr, or —COI, wherein X and Y are independently H, or linear or branched $C_1$-$C_8$-alkyl, optionally substituted with halogens and optionally polymer-supported; and $R_4$=—H, linear or branched $C_1$-$C_8$-alkyl, —CH=CH$_2$, —CO$_2$X, —C(O)NX$_2$, —CH$_2$OX, —CH$_2$NX$_2$, —CHO, —OX, —CN, —NO$_2$, —C(O)NX, —C(=NY)X, —CF$_3$, —CCl$_3$, —CBr$_3$, —CI$_3$, —SO$_2$X, —SO$_3$X, —NX$_2$, —COX, —COF, —COCl, —COBr, or —COI, wherein X and Y are independently H, or linear or branched $C_1$-$C_8$-alkyl, optionally substituted with halogens and optionally polymer-supported.

For instance, compounds Va and/or Vb wherein $R_4$=Me or $CH_2OH$ may be obtained from IIIa, IIIb, IIIc and/or IIId in a reduction reaction. Compound Va and/or Vb wherein $R_4$=$CO_2H$ may be obtained from IIIa, IIIb, IIIc and/or IIId in a hydrolysis reaction. Compound Va and/or Vb wherein $R_4$=H and $R_3$=H may be obtained from IIIa, IIIb, IIIc or IIId in a hydrolysis and a subsequent decarboxylation reaction.

In another embodiment of the present invention, the bicyclic adduct is reacted, before ring-opening in a reaction that is one or more selected from the group consisting of hydrolysis, oxidation, reduction, displacement reactions such as nucleophilic addition, olefination, rearrangement, decarboxylation and combinations thereof.

For instance, the bicyclic adduct wherein one or more of $R_1$, $R_2$, $R_3$, or EWG is an ester may be (partially) hydrolyzed to yield carboxylic acids. It will be appreciated that any method wherein an intermediate reaction step is performed before the bicyclic product is ring-opened lies within the scope of the present invention.

For the purpose of clarity and a concise description, features are described herein as part of the same or separate embodiments. However, it will be appreciated that the scope of the invention may include embodiments having combinations of all or some of the features described.

The invention may further be illustrated by the following examples. It may be appreciated that each of the substrate compounds (i.e. furanic compound, dienophile or phenolic compound) that are used in the examples below may also be converted to to these or other phenolic products under different reaction conditions (e.g. with different reagents) as specified and that the specified reaction conditions are therefore not to be interpreted as limiting the present invention.

EXAMPLE 1

Step 1. Synthesis of methyl 2-methyl-5-hydroxy-benzoate

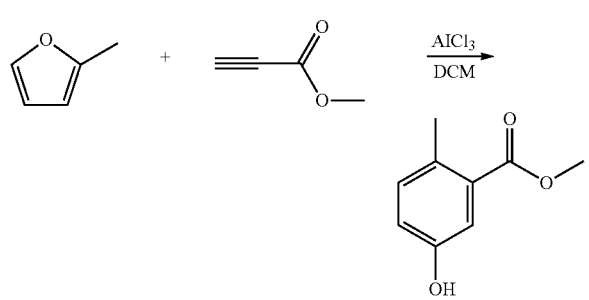

A reactor was charged with dichloromethane (DCM, 62 ml), then aluminium chloride (2 g) was added in portions over about 60 seconds. This suspension was stirred for 10 minutes and then methyl propiolate (1261 mg, 1334 µL) was added and the mixture stirred for a further 10 minutes. A solution of 2-methylfuran (1237 mg, 1359 µL) in DCM (12.4 ml) was added dropwise over about 30 minutes. After complete addition, the reaction mixture was allowed to stir for 50 minutes at room temperature. The reaction mixture was poured into a stirred mixture of ice (20 g) and water (60 ml). The organics were separated and then the aqueous solution was extracted with DCM (80 ml). The combined organics were washed with water and dried ($Na_2SO_4$), and filtered. The organic solution was reduced by rotary evaporation to yield an oil, which was purified on a Revelris® X2 Flash Chromatography System, eluting with n-hexane and ethyl acetate. Appropriate fractions were collected for the product peak and were reduced by rotary evaporation to obtain the desired product as a yellow solid (887 mg, 36%).

The structure was confirmed as methyl 2-methyl-5-hydroxy-benzoate by 1H NMR (see FIG. 1).

Step 2. Synthesis of 2-methyl-5-hydroxy-benzoic Acid

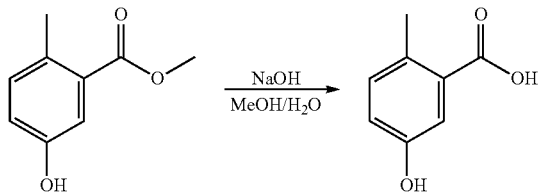

Figure 2:
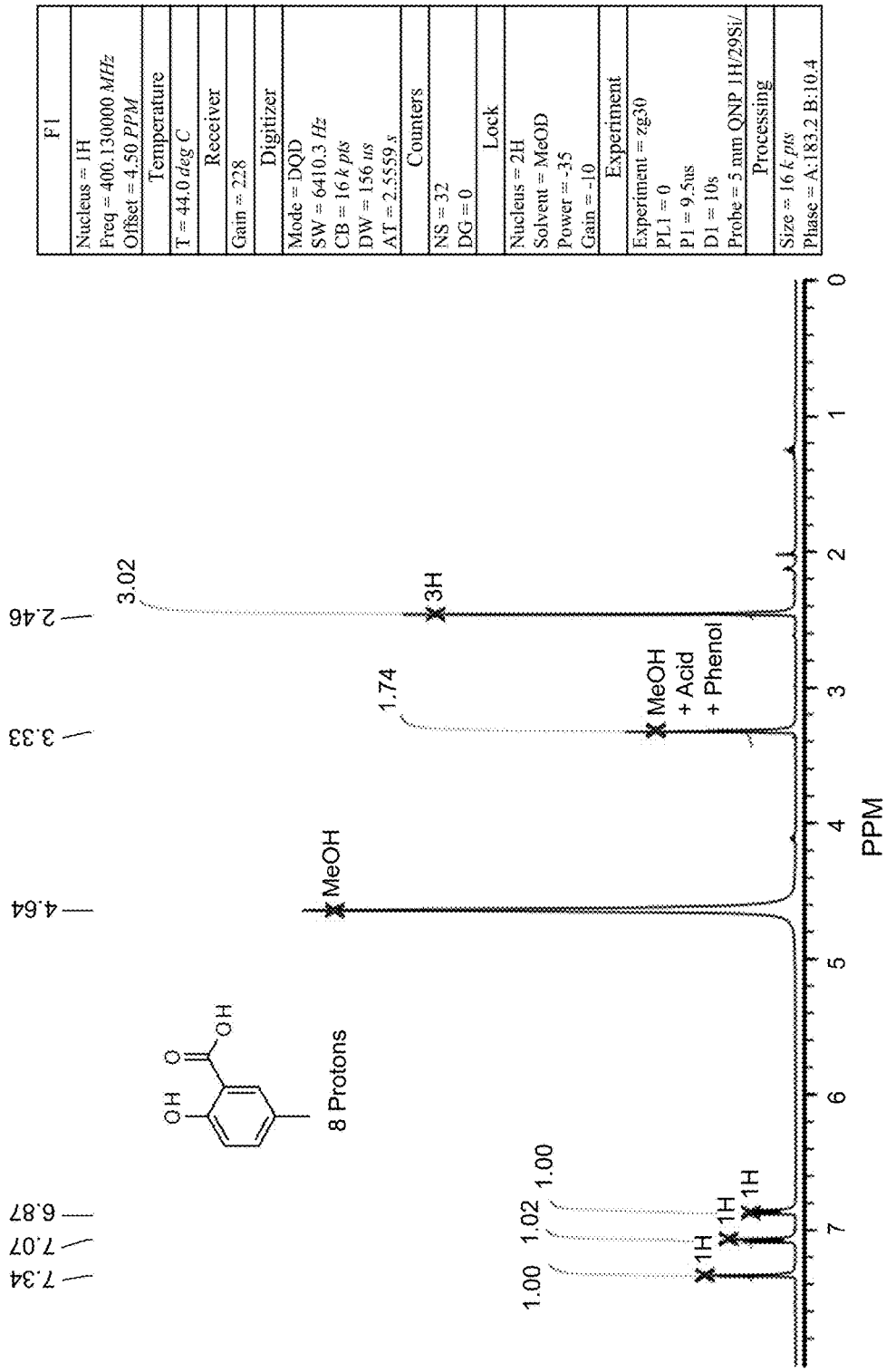
FIG. 2 is an NMR spectrum of 2-methyl-5-hydroxy-benzoic acid which is another compound obtained in accordance with the present invention.

Sodium hydroxide (600 mg) was dissolved in water (15 ml). A reactor was charged with methyl 2-methyl-5-hydroxy-benzoate (800 mg, 4.8 mmol), then methanol (15 ml) was added. The solid was dissolved with stirring to give a yellow solution. The NaOH solution was added to the methanol solution, and the reaction mixture was heated to 45° C. and held for 4 hours. The reaction mixture was washed with DCM (2×30 ml). The aqueous layer was acidified to pH~2 with 1M HCl (aq.) solution, then the organics were extracted twice with EtOAc (2×30 ml). The combined organics were dried ($Na_2SO_4$), filtered and reduced to yield a yellow solid (642 mg, 88%). The structure was confirmed as 2-methyl-5-hydroxy-benzoic acid by 1H NMR (see FIG. 2).

Step 3. Synthesis of p-cresol

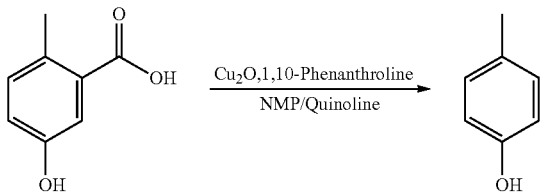

Figure 3:
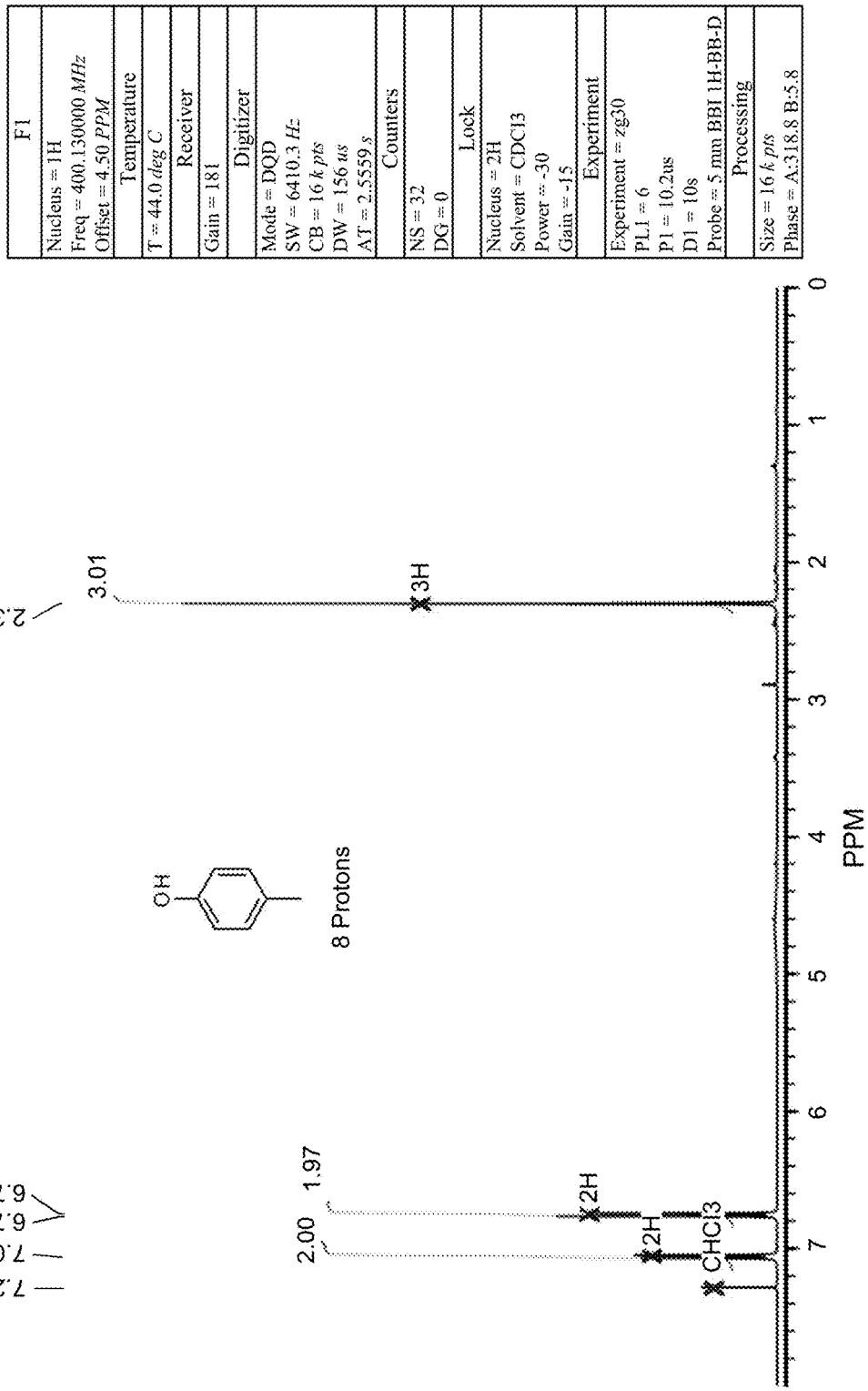
FIG. 3 is an NMR spectrum of p-cresol which is yet another compound obtained in accordance with the present invention.

A reactor was charged with 2-methyl-5-hydroxy-benzoic acid (100 mg), copper(I) oxide (4.8 mg), 1,10-phenanthroline (11.8 mg), NMP (1000 µL) and quinoline (333 µL). The reactor was sealed, heated to 170° C., and held for 19 hours, with stirring. After cooling, analysis showed a significant amount of remaining starting material (>50%). Fresh copper (I) oxide (4.8 mg) and 1,10-phenanthroline (11.8 mg) were added. The reactor was re-sealed, heated to 170° C. and held for a further 19 hours, with stirring. The reaction mixture was brought directly onto silica and purified on a Revelris® X2 Flash Chromatography System, eluting with n-hexane and ethyl acetate. Appropriate fractions were collected for the product peak and were reduced by rotary evaporation to obtain the desired product as a yellow liquid. Analysis showed this to contain significant levels of quinolone. The sample was dissolved in DCM (10 ml) and this was washed twice with 1N HCl solution (10 ml). The organics were then washed with water (10 ml), dried (Na$_2$SO$_4$), filtered, and reduced to yield a slightly yellow oil (43 mg, 61%). The structure was confirmed as p-cresol by 1H NMR (see FIG. 3).

EXAMPLE 2. Synthesis of methyl 2-hydroxybenzoate and methyl 3-hydroxybenzoate

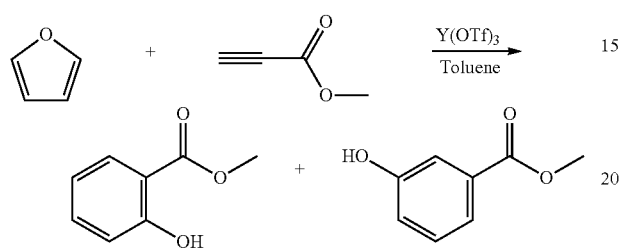

A reactor was charged with yttrium triflate (105 mg), and then toluene (1.5 ml) and methyl propiolate (227 mg, 240 μL) were added. This was stirred for 30 minutes then furan (211 mg, 225 μL) was added. The reactor was sealed, heated to 135° C. and held for 14 hours with stirring. The reaction mixture was cooled to room temperature and water (10 ml) was added. The organics were separated and the aqueous phase was extracted with toluene (2×10 ml). The combined organics were washed with water (10 ml), dried (Na$_2$SO$_4$), filtered and reduced to yield a brown oil (226 mg, 56%). Analysis by NMR confirmed this to be a very clean mixture of the two regio-isomeric products methyl 2-hydroxybenzoate and methyl 3-hydroxybenzoate in around a 1:1 ratio. The structure was confirmed as a very clean mixture of the two regio-isomeric products methyl 2-hydroxybenzoate and methyl 3-hydroxybenzoate in around a 1:1 ratio, by 1H NMR.

EXAMPLE 3 Synthesis of methyl 5-hydroxy-2-methylbenzoate

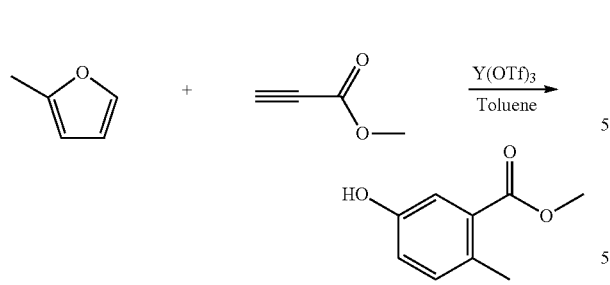

A reactor was charged with yttrium triflate (48 mg), and then toluene (0.3 ml) and methyl propiolate (151 mg, 160 μL) were added. The reactor was sealed, heated to 150° C. with stirring. 2-Methylfuran (157 mg, 172 μL) was added continuously over a 3 hour period. The reaction mixture was cooled to room temperature and water (10 ml) was added. The organics were separated and the aqueous phase was extracted with toluene (2×10 ml). The combined organics were washed with water (10 ml), dried (Na$_2$SO$_4$) and filtered. The organic solution was reduced by rotary evaporation to yield an oil, which was purified on a Reveleris® X2 Flash Chromatography System, eluting with n-hexane and ethyl acetate. Appropriate fractions were collected for the product peak and were reduced by rotary evaporation to obtain the desired product as a light brown solid (354 mg, 79%). The structure was confirmed as methyl 5-hydroxy-2-methylbenzoate by 1H NMR.

EXAMPLE 4 Synthesis of 5-hydroxy-2-methylbenzoic Acid

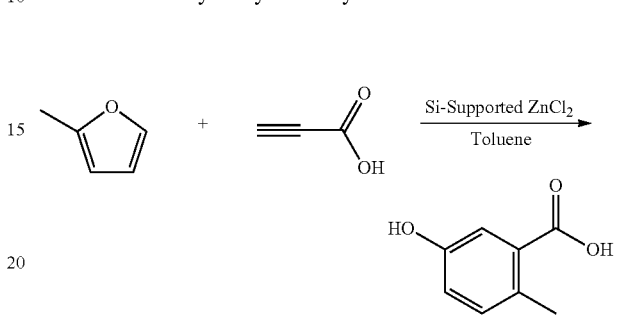

A reactor was charged with zinc chloride supported on silica (195 mg), and then propiolic acid (175 mg, 154 μL) and 2-methylfuran (461 mg, 1 mL) were charged, and the reactor was sealed, and heated to 100° C. with stirring, and held for 16 hours. The reaction mixture was cooled to room temperature and water (10 ml) was added. The organics were extracted with dichloromethane (2×10 ml), and the combined organics were washed with water (10 ml), dried (Na$_2$SO$_4$) and filtered. The organic solution was reduced by rotary evaporation to yield an oil, which was purified on a Reveleris® X2 Flash Chromatography System, eluting with n-hexane and ethyl acetate. Appropriate fractions were collected for the product peak and were reduced by rotary evaporation to obtain the desired product as a light yellow oil (19 mg, 5%). The structure was confirmed as 5-hydroxy-2-methylbenzoic acid by 1H NMR.

EXAMPLE 5 Synthesis of 1-(5-hydroxy-2-methylphenyl)-ethanone

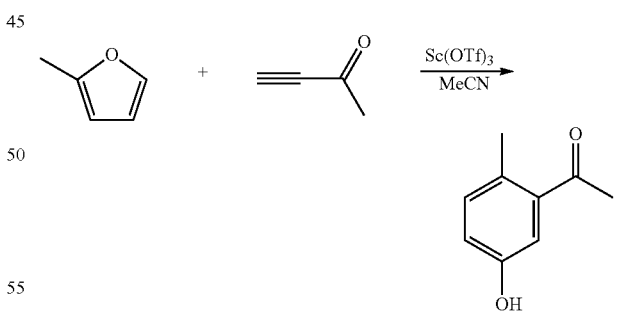

A reactor was charged with scandium triflate (277 mg), and then acetonitrile (3 ml) and 3-butyn-2-one (382 mg, 440 μL) were added and the contents stirred for 10 minutes at ambient temperature. 2-Methylfuran (461 mg, 507 μL) was then charged, and the reactor was sealed, and heated to 100° C. with stirring, and held for 60 hours. The reaction mixture was cooled to room temperature and water (10 ml) was added. The organics were extracted with dichloromethane (2×10 ml), and the combined organics were washed with water (10 ml), dried (Na$_2$SO$_4$) and filtered. The organic solution was reduced by rotary evaporation to yield an oil, which was purified on a Reveleris® X2 Flash Chromatography System, eluting with n-hexane and ethyl acetate. Appropriate fractions were collected for the product peak and were reduced by rotary evaporation to obtain the desired product as a light yellow oil (34 mg, 4%). The structure was confirmed as 1-(5-hydroxy-2-methylphenyl)-ethanone by 1H NMR.

EXAMPLE 6 Synthesis of methyl 2-bromo-5-hydroxybenzoate

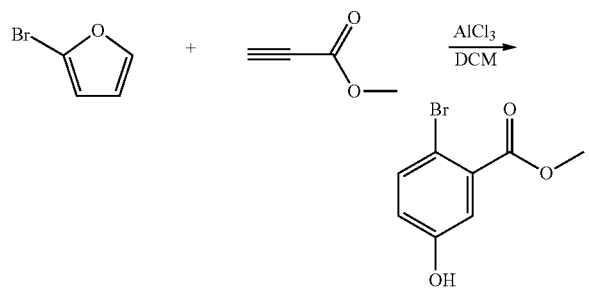

A reactor was charged with dichloromethane (2.325 ml) then aluminium chloride (100 mg) was added in portions over about 60 seconds. This was stirred for 10 minutes then methyl propiolate (63.0 mg, 66.7 µL) was added, and the mixture stirred for 10 more minutes. A solution of 2-bromofuran (110.2 mg, 66.3 µL) in dichloromethane (0.465 ml) was added dropwise over ~30 minutes. After complete addition, the reaction was stirred 50 minutes at ambient temperature. The reaction mixture was poured into a stirred mixture of ice (50 g) and water (10 ml). The organics were separated then the aqueous extracted with dichloromethane (10 ml). The combined organics were washed with water (10 ml), dried (Na₂SO₄), and filtered. The organic solution was reduced by rotary evaporation to yield an oil, which was purified on a Reveleris® X2 Flash Chromatography System, eluting with n-hexane and ethyl acetate. Appropriate fractions were collected for the product peak and were reduced by rotary evaporation to obtain the desired product as a clear oil (47 mg, 27%). The structure was confirmed as methyl 2-bromo-5-hydroxybenzoate by 1H NMR.

EXAMPLE 7 Synthesis of methyl 2-hydroxy-3,5-dimethylbenzoate, methyl 3-hydroxy-2,6-dimethylbenzoate and methyl 5-hydroxy-2,4-dimethylbenzoate

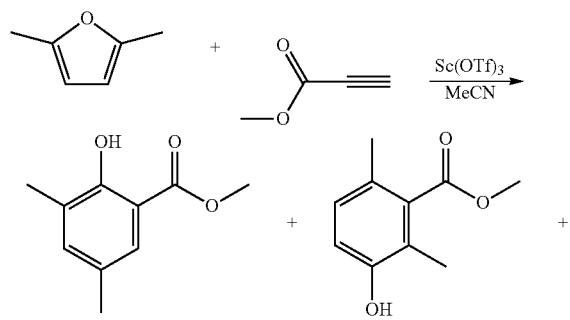

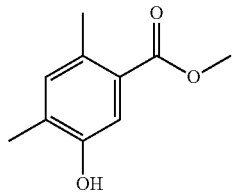

A reactor was charged with scandium triflate (277 mg), and then acetonitrile (3 ml) and methyl propiolate (472 mg, 500 µL) were added and the contents stirred for 10 minutes at ambient temperature. 2,5-Dimethylfuran (540 mg, 607 µL) was then charged, and the reactor was sealed, and heated to 100° C. with stirring, and held for 60 hours. The reaction mixture was cooled to room temperature and water (10 ml) was added. The organics were extracted with dichloromethane (2×10 ml), and the combined organics were washed with water (10 ml), dried (Na₂SO₄) and filtered. The organic solution was reduced by rotary evaporation to yield an oil, which was purified on a Reveleris® X2 Flash Chromatography System, eluting with n-hexane and ethyl acetate. Appropriate fractions were collected for the 2 product peaks and these were reduced by rotary evaporation to obtain a white solid (101 mg, 10%) and yellow oil (232 mg, 23%). The first was confirmed as methyl 2-hydroxy-3,5-dimethylbenzoate by 1H NMR. The second was confirmed as a ~1:6:2 mixture of 2-hydroxy-3,5-dimethylbenzoate, methyl 3-hydroxy-2,6-dimethylbenzoate and methyl 5-hydroxy-2,4-dimethylbenzoate by 1H NMR.

EXAMPLE 8 Synthesis of dimethyl 3-hydroxy-6-methylbenzene-1,2-dicarboxylate

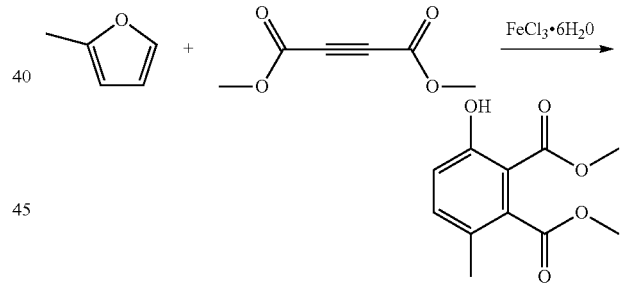

A reactor was charged with iron(III) chloride hexahydrate (220 mg), and then dimethyl acetylenedicarboxylate (1156 mg, 1000 µL) was added and the contents stirred for 10 minutes at ambient temperature. 2-Methylfuran (668 mg, 720 µL) was then charged, and the reactor was sealed, and heated to 150° C. with stirring, and held for 2 hours. The reaction mixture was cooled to room temperature and water (10 ml) was added. The organics were extracted with dichloromethane (2×10 ml), and the combined organics were washed with water (10 ml), dried (Na₂SO₄) and filtered. The organic solution was reduced by rotary evaporation to yield an oil, which was purified on a Reveleris® X2 Flash Chromatography System, eluting with n-hexane and ethyl acetate. Appropriate fractions were collected for the product peak and were reduced by rotary evaporation to obtain the desired product as a light yellow oil (511 mg, 28%). The structure was confirmed as dimethyl 3-hydroxy-6-methyl-benzene-1,2-dicarboxylate by 1H NMR.

EXAMPLE 9 Synthesis of dimethyl 3-hydroxy-4,6-dimethyl-1,2-benzenedicarboxylate and dimethyl 4-hydroxy-3,6-dimethyl-1,2-benzenedicarboxylate

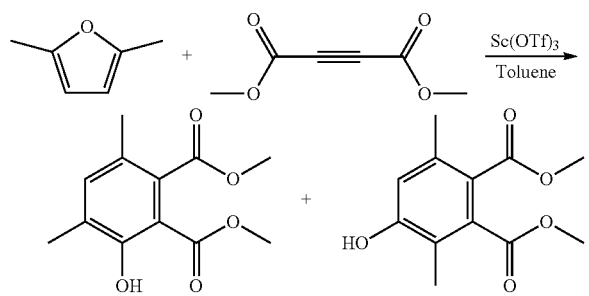

A reactor was charged with scandium triflate (277 mg), and then toluene (3 ml) and dimethyl acetylenedicarboxylate (799 mg, 691 μL) were added and the contents stirred for 10 minutes at ambient temperature. 2,5-Dimethylfuran (540 mg, 607 μL) was then charged, and the reactor was sealed, and heated to 100° C. with stirring, and held for 60 hours. The reaction mixture was cooled to room temperature and water (10 ml) was added. The organics were extracted with dichloromethane (2×10 ml), and the combined organics were washed with water (10 ml), dried (Na$_2$SO$_4$) and filtered. The organic solution was reduced by rotary evaporation to yield an oil, which was purified on a Reveleris® X2 Flash Chromatography System, eluting with n-hexane and ethyl acetate. Appropriate fractions were collected for the product peak and were reduced by rotary evaporation to obtain two clear oils (228 mg, 17% and 202 mg, 15%). The structure of the first was confirmed as dimethyl 3-hydroxy-4,6-dimethyl-1,2-benzenedicarboxylate by 1H NMR. The structure of the second was confirmed as dimethyl 4-hydroxy-3,6-dimethyl-1,2-benzenedicarboxylate by 1H NMR.

EXAMPLE 11 Synthesis of dimethyl 3-(ethoxymethyl)-6-hydroxy-1,2-benzenedicarboxylate

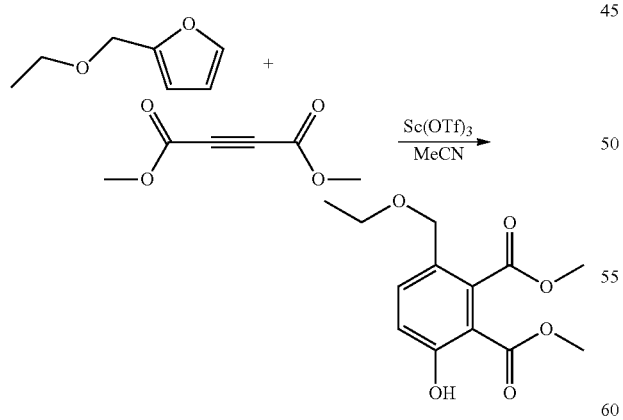

A reactor was charged with scandium triflate (277 mg), and then acetonitrile (3 ml) and dimethyl acetylenedicarboxylate (799 mg, 691 μL) were added and the contents stirred for 10 minutes at ambient temperature. 2-(ethoxymethyl)furan (710 mg, 720 μL) was then charged, and the reactor was sealed, and heated to 100° C. with stirring, and held for 16 hours. The reaction mixture was cooled to room temperature and water (10 ml) was added. The organics were extracted with dichloromethane (2×10 ml), and the combined organics were washed with water (10 ml), dried (Na$_2$SO$_4$) and filtered. The organic solution was reduced by rotary evaporation to yield an oil, which was purified on a Reveleris® X2 Flash Chromatography System, eluting with n-hexane and ethyl acetate. Appropriate fractions were collected for the product peak and were reduced by rotary evaporation to obtain the desired product as a light yellow oil (482 mg, 32%). The structure was confirmed as dimethyl 3-(ethoxymethyl)-6-hydroxy-1,2-benzenedicarboxylate by 1H NMR.

EXAMPLE 12 Synthesis of 3-hydroxy-6-methylbenzene-1,2-dicarboxylic Acid

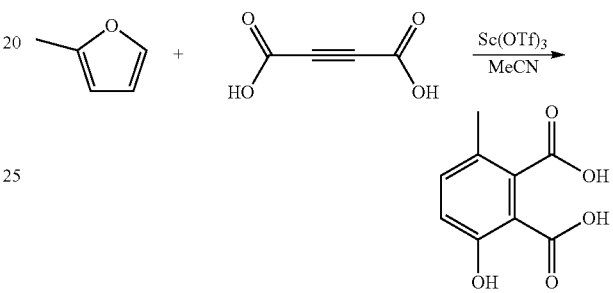

A reactor was charged with zinc chloride supported on silica (195 mg), and then dimethyl acetylenedicarboxylate (355 mg, 307 μL) and 2-methylfuran (461 mg, 1 mL) were charged, and the reactor was sealed, and heated to 100° C. with stirring, and held for 16 hours. The reaction mixture was cooled to room temperature and water (10 ml) was added. The organics were extracted with dichloromethane (2×10 ml), and the combined organics were washed with water (10 ml), dried (Na$_2$SO$_4$) and filtered. The organic solution was reduced by rotary evaporation to yield an oil, which was purified on a Reveleris® X2 Flash Chromatography System, eluting with n-hexane and ethyl acetate. Appropriate fractions were collected for the product peak and were reduced by rotary evaporation to obtain the desired product as a yellow oil (123 mg, 25%). The structure was confirmed as 3-hydroxy-6-methylbenzene-1,2-dicarboxylic acid by 1H NMR.

EXAMPLE 13 Synthesis of dimethyl 7-oxabicyclo[2.2.1]hepta-2,5-diene-2,3-dicarboxylate

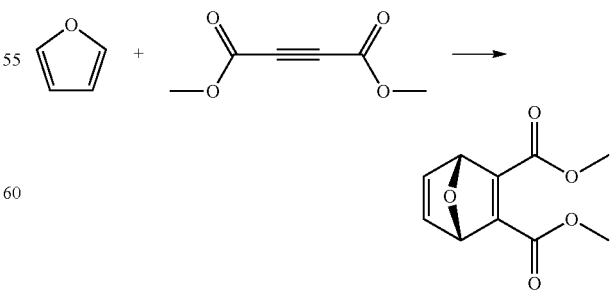

A reactor was charged with dimethyl acetylenedicarboxylate (1156 mg, 1000 μL) and furan (553.7 mg, 591.6 μL). The reactor was sealed and heated to 100° C. and held for 2 hours. The reaction mixture was cooled to room temperature and then reduced by rotary evaporation to yield an oil, which was purified on a Reveleris® X2 Flash Chromatography System, eluting with n-hexane and ethyl acetate. Appropriate fractions were collected for the product peak and were reduced by rotary evaporation to obtain the desired product as a light yellow liquid (960 mg, 56%). The structure was confirmed as dimethyl 7-oxabicyclo[2.2.1]hepta-2,5-diene-2,3-dicarboxylate by 1H NMR.

EXAMPLE 14 Synthesis of dimethyl 1-methyl-7-oxabicyclo[2.2.1]hepta-2,5-diene-2,3-dicarboxylate

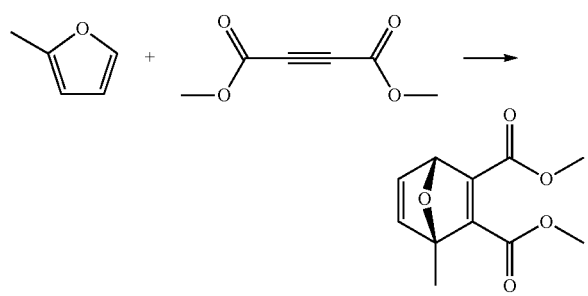

A reactor was charged with dimethyl acetylenedicarboxylate (1156 mg 1000 μL) and 2-methylfuran (668 mg, 720 μL). The reactor was sealed, and the reaction heated to 120° C. and held for 2 hours with stirring. The reaction mixture was cooled to room temperature then purified on a Reveleris® X2 Flash Chromatography System, eluting with n-hexane and ethyl acetate. Appropriate fractions were collected for the product peak and were reduced by rotary evaporation to obtain the desired product as a light yellow solid (1660 mg, 91%). The structure was confirmed as dimethyl 1-methyl-7-oxabicyclo[2.2.1]hepta-2,5-diene-2,3-dicarboxylate by 1H NMR.

EXAMPLE 15 Synthesis of dimethyl 3-hydroxy-6-methylbenzene-1,2-dicarboxylate

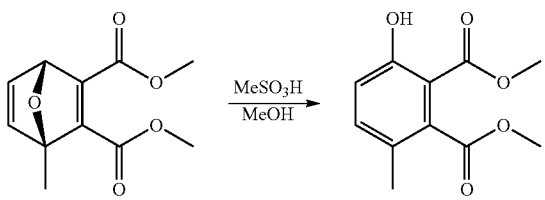 [SMILES: "MeSO3H" ; "MeOH" ; COC(=O)C1=C(C(=O)OC)[C@]2(C)C=C[C@H]1O2 ; COC(=O)c1c(C)ccc(O)c1C(=O)OC]

A reactor was charged with dimethyl 1-methyl-7-oxabicyclo[2.2.1]hepta-2,5-diene-2,3-dicarboxyate (200 mg), methanol (549 μL) and methanesulfonic acid (668 mg, 451 μL). The reactor was sealed, and the reaction heated to 147° C. and held for 9.5 minutes with stirring. The reaction mixture was cooled to room temperature then purified on a Reveleris® X2 Flash Chromatography System, eluting with n-hexane and ethyl acetate. Appropriate fractions were collected for the product peak and were reduced by rotary evaporation to obtain the desired product as a light yellow solid (188 mg, 94%). The structure was confirmed as dimethyl 3-hydroxy-6-methylbenzene-1,2-dicarboxylate by 1H NMR.

EXAMPLE 16 Synthesis of dimethyl 3-hydroxy-6-methylbenzene-1,2-dicarboxylate

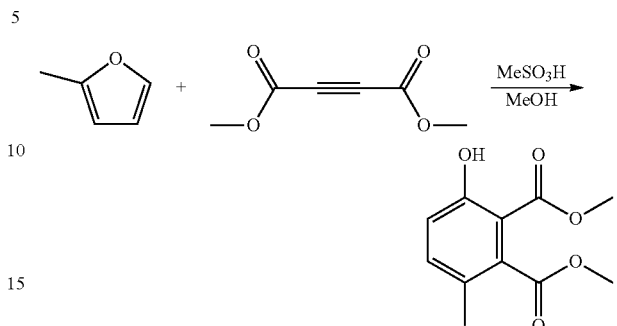

2-Methylfuran and dimethyl acetylenedicarboxylate were charged into a tubular reactor in a 1:1 molar ratio. After a residence time of 6 minutes at 120° C., a 7.0M solution of methanesulfonic acid in methanol was charged at 2 times the volume of the combined 2-methylfuran/dimethyl acetylenedicarboxylate flow. The reaction mixture was then directly heated to 150° C. and held for 2 minutes. The mixture exiting the reactor was quenched directing into a 1:1 mixture of ice:1M aqueous sodium hydroxide. The organics were extracted twice with dichloromethane, and the combined organics were washed with water, dried ($Na_2SO_4$) and filtered. The organic solution was reduced by rotary evaporation to yield a brown oil (73%). The structure was confirmed as dimethyl 3-hydroxy-6-methylbenzene-1,2-dicarboxylate by 1H NMR.

EXAMPLE 17 Synthesis of dimethyl 1,4-dimethyl-7-oxabicyclo[2.2.1]hepta-2,5-diene-2,3-dicarboxylate

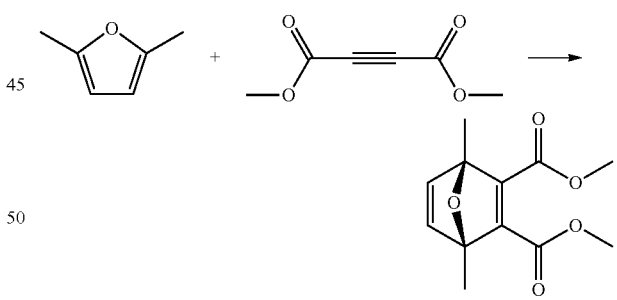

A reactor was charged with dimethyl acetylenedicarboxylate (1156 mg, 1000 μL) and 2,5-dimethylfuran (782.0 mg, 878.6 μL). The reactor was sealed and the heated to 100° C. and held for 2 hours. The reaction mixture was cooled to room temperature and then reduced by rotary evaporation to yield an oil, which was purified on a Reveleris® X2 Flash Chromatography System, eluting with n-hexane and ethyl acetate. Appropriate fractions were collected for the product peak and were reduced by rotary evaporation to obtain the desired product as a light yellow liquid (1.51 g, 78%). The structure was confirmed as dimethyl 1,4-dimethyl-7-oxabicyclo[2.2.1]hepta-2,5-diene-2,3-dicarboxylate by 1H NMR.

EXAMPLE 18 Synthesis of dimethyl 3-hydroxy-4,6-dimethyl-1,2-benzenedicarboxylate and dimethyl 4-hydroxy-3,6-dimethyl-1,2-benzenedicarboxylate

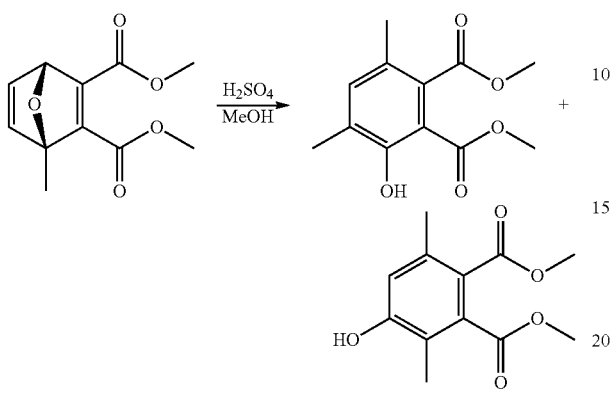

A reactor was charged with dimethyl 1,4-dimethyl-7-oxabicyclo[2.2.1]hepta-2,5-diene-2,3-dicarboxylate (500 mg) and methanol (10 ml) and this was stirred until solution was achieved. Concentrated sulfuric acid (500 µL) was then added dropwise. The reactor was sealed and heated to 150° C., with stirring, in a microwave for 10 minutes. The reaction mixture was then reduced by rotary evaporation to yield an oil. This was dissolved in dichloromethane (10 ml) and then the solution was washed with saturated aqueous sodium bicarbonate solution (5 ml), and then water (5 ml). The organic phase was then dried (Na$_2$SO$_4$), filtered and reduced to yield an oil, which was purified on a Reveleris® X2 Flash Chromatography System, eluting with n-hexane and ethyl acetate. Appropriate fractions were collected for the product peak and were reduced by rotary evaporation to obtain two clear oils (230 mg, 46% and 217 mg, 43%). The structure of the first was confirmed as dimethyl 3-hydroxy-4,6-dimethyl-1,2-benzenedicarboxylate by 1H NMR. The structure of the second was confirmed as dimethyl 4-hydroxy-3,6-dimethyl-1,2-benzenedicarboxylate by 1H NMR.

EXAMPLE 19 Synthesis of dimethyl 4-(ethoxymethyl)-7-oxabicyclo[2.2.1]hepta-2,5-diene-2,3-dicarboxylate

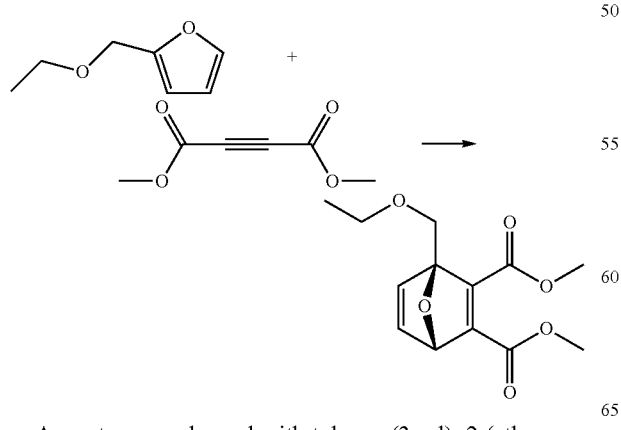

A reactor was charged with toluene (3 ml), 2-(ethoxymethyl)furan (709.6 mg, 720.4 µL) and dimethyl acetylenedicarboxylate (798.7 mg, 690.9 µL). The reactor was sealed, and the reaction heated to 100° C. and held for 16 hours with stirring. The reaction mixture was cooled to room temperature and then reduced by rotary evaporation to yield an oil, which was purified on a Reveleris® X2 Flash Chromatography System, eluting with n-hexane and ethyl acetate. Appropriate fractions were collected for the product peak and were reduced by rotary evaporation to obtain the desired product as a light brown oil (969 mg, 64%). The structure was confirmed as dimethyl 4-(ethoxymethyl)-7-oxabicyclo [2.2.1]hepta-2,5-diene-2,3-dicarboxylate by 1H NMR.

EXAMPLE 20 Synthesis of dimethyl 3-(ethoxymethyl)-6-hydroxybenzene-1,2-dicarboxylate

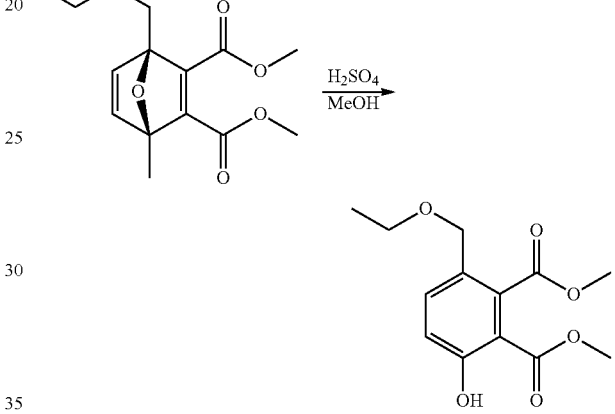

A reactor was charged with dimethyl 4-(ethoxymethyl)-7-oxabicyclo[2.2.1]hepta-2,5-diene-2,3-dicarboxylate (100 mg) and methanol (4 ml) and this was stirred until solution was achieved. Concentrated sulfuric acid (100 µL) was then added dropwise. The reactor was sealed and the reaction left to stir for 60 minutes at ambient temperature. The reaction mixture was then reduced by rotary evaporation to yield an oil. This was dissolved in dichloromethane (2 ml), and then the solution was washed with saturated aqueous sodium bicarbonate solution (5 ml), and then water (5 ml). The organic phase was then dried (Na$_2$SO$_4$), filtered and reduced to yield an oil, which was purified on a Reveleris® X2 Flash Chromatography System, eluting with n-hexane and ethyl acetate. Appropriate fractions were collected for the product peak and were reduced by rotary evaporation to obtain the desired product as a clear oil (31 mg, 31%). The structure was confirmed as dimethyl 3-(ethoxymethyl)-6-hydroxybenzene-1,2-dicarboxylate by 1H NMR.

EXAMPLE 21 Synthesis of methyl 2-tert-butyl-5-hydroxybenzoate or methyl 5-tert-butyl-2-hydroxybenzoate

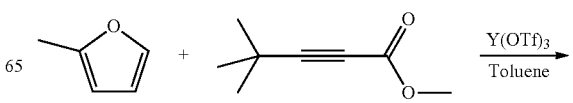

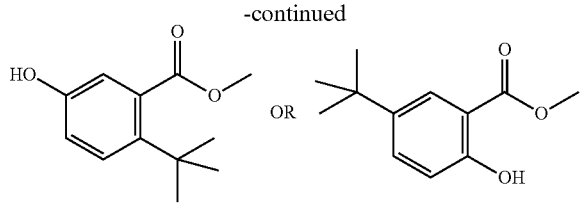

A reactor was charged with yttrium triflate (100.5 mg) and then toluene (1 ml) and methyl 4,4-dimethyl-2-pentynoate (262.8 mg) were added. This was stirred for 10 minutes at room temperature and then 2-methylfuran (169.3 mg, 153.9 µL) was added. The reactor was sealed and heated to 120° C. for 2 hours. The reaction mixture was cooled to room temperature and water (10 ml) was added. The organics were separated and the aqueous phase was extracted with toluene (2×10 ml). The combined organics were washed with water (10 ml), dried (Na$_2$SO$_4$) and filtered. The organic solution was reduced by rotary evaporation to yield an oil, which was purified on a Reveleris® X2 Flash Chromatography System, eluting with n-hexane and ethyl acetate. Appropriate fractions were collected for the product peak and were reduced by rotary evaporation to obtain the desired product as a light brown solid (7 mg, 2%). The structure was confirmed as either 2-tert-butyl-5-hydroxybenzoate or methyl 5-tert-butyl-2-hydroxybenzoate by 1H NMR, but the exact regionisomer could not be determined.

EXAMPLE 22 Synthesis of 2-hydroxybenzoic Acid

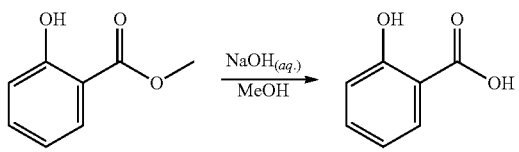

A reactor was charged with methyl 2-hydroxybenzoate (722 mg), sodium hydroxide (1.9 g) and water (20 ml). The reactor was sealed and the biphasic mixture was stirred for 48 hours at ambient temperature. The resulting clear solution was acidified to pH 1 with concentrated hydrochloric acid, which caused a white solid to precipitate. This was filtered and washed with water (20 ml) and then dried for 16 hours at 50° C. and 100 mBar. This yielded the desired product as a white solid (601 mg, 92%). The structure was confirmed as 2-hydroxybenzoic acid by 1H NMR.

EXAMPLE 23 Synthesis of 5-hydroxy-2-methylbenzoic Acid

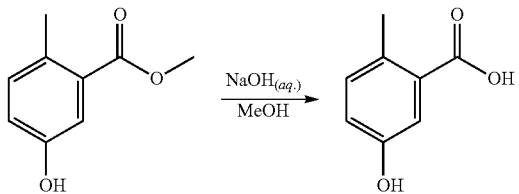

A reactor was charged with methyl 5-hydroxy-2-methylbenzoate (800 mg) and then methanol (15 ml) was added, and this mixture was stirred until the solid was dissolved. Sodium hydroxide (600 mg) was dissolved in water (15 ml), and this solution was added to the methanol solution and the reaction mixture was heated to 45° C. and held for 4 hours. The reaction mixture was washed with dichloromethane (2×30 ml). The aqueous layer was acidified to pH~2 with 1M aqueous hydrochloric acid solution and then the organics were extracted twice with ethyl acetate (2×30 ml). The combined organics were dried (Na$_2$SO$_4$), filtered and reduced to yield a yellow solid (642 mg, 88%). The structure was confirmed as 5-hydroxy-2-methylbenzoic acid by 1H NMR.

EXAMPLE 24 Synthesis of 2-hydroxybenzamide

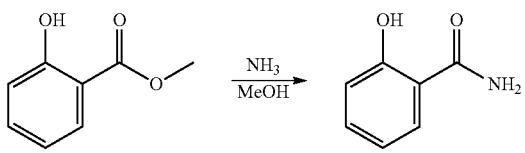

To a reactor was charged methyl 2-hydroxybenzoate (160 mg) and 7N ammonia in methanol (4 ml). The reactor was then sealed, heated to 50° C., and stirred for 16 hours. The reaction mixture was cooled to ambient temperature then reduced by rotary evaporation to yield an oil. This was purified by flash chromatography, eluting with n-hexane and ethyl acetate. Appropriate fractions were collected for the product peak and were reduced by rotary evaporation to obtain the desired product as yellow oil (135 mg, 94%). The structure was confirmed as 2-hydroxybenzamide by 1H NMR.

EXAMPLE 25 Synthesis of 3-hydroxybenzamide

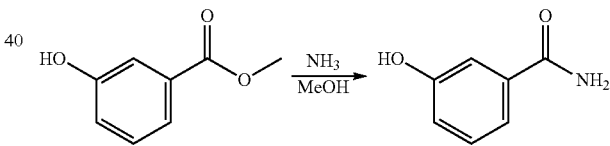

To a reactor was charged methyl 3-hydroxybenzoate (160 mg) and 7N ammonia in methanol (4 ml). The reactor was then sealed, heated to 50° C., and stirred for 16 hours. The reaction mixture was cooled to ambient temperature then reduced by rotary evaporation to yield an oil. This was purified by flash chromatography, eluting with n-hexane and ethyl acetate. Appropriate fractions were collected for the product peak and were reduced by rotary evaporation to obtain the desired product as yellow oil (15 mg, 10%). The structure was confirmed as 3-hydroxybenzamide by 1H NMR.

EXAMPLE 26 Synthesis of Methyl Benzoate

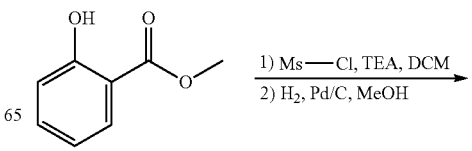

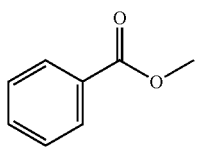

A reactor was charged with methyl 2-hydroxybenzoate (1.55 g) and a solution of triethylamine (1.45 g, 2 ml) dissolved in dichloromethane (50 ml). The reactor was sealed and the mixture cooled to 0° C. Methanesulfonyl chloride (1.92 g, 1.3 ml) was then charged dropwise over 20 minutes. After addition the mixture was allowed to warm to ambient temperature and stir for a further 60 minutes. The solution was then washed with a saturated aqueous sodium chloride solution (2×25 ml) and then a 10% aqueous sodium bicarbonate solution (25 ml). The organic layer was dried (MgSO$_4$), filtered and reduced to an oil by rotary evaporation. This was purified by flash chromatography, eluting with n-hexane and ethyl acetate. Appropriate fractions were collected for the product peak and were reduced by rotary evaporation to obtain a clear oil (2.2 g, 96%). The structure was confirmed as methyl 2-methylsulfonyloxybenzoate by 1H NMR.

To a reactor was charged methyl 2-methylsulfonyloxybenzoate (0.54 g) and methanol (4.6 ml), and this was stirred until dissolved. 10% palladium on charcoal (56 mg) and diethylamine (230 mg, 325.3 µL) were then charged. The reactor was sealed then the atmosphere was flushed with hydrogen gas. The reaction was stirred at ambient temperature for 16 hours under a positive pressure of hydrogen gas. After removal of the hydrogen atmosphere, the mixture was filtered through a 0.45 µm filter. Dichloromethane (20 ml) and water (10 ml) were then charged to the methanolic solution, and the mixture vigorously mixed. The organic phase was separated and the aqueous phase was extracted with dichloromethane (2×10 ml). The combined organic phase was dried (MgSO$_4$), filtered and reduced to an oil by rotary evaporation. This was purified by flash chromatography, eluting with n-hexane and ethyl acetate. Appropriate fractions were collected for the product peak and were reduced by rotary evaporation to obtain a clear liquid (297 mg, 93%). The structure was confirmed as methyl benzoate by 1H NMR.

EXAMPLE 27 Synthesis of Methyl Benzoate

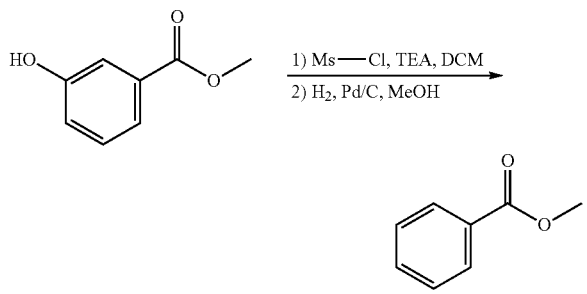

A reactor was charged with methyl 3-hydroxybenzoate (1.55 g) and a solution of triethylamine (1.45 g, 2 ml) dissolved in dichloromethane (50 ml). The reactor was sealed and the mixture cooled to 0° C. Methanesulfonyl chloride (1.92 g, 1.3 ml) was then charged dropwise over 20 minutes. After addition the mixture was allowed to warm to ambient temperature and stir for a further 60 minutes. The solution was then washed with a saturated aqueous sodium chloride solution (2×25 ml) and then a 10% aqueous sodium bicarbonate solution (25 ml). The organic layer was dried (MgSO$_4$), filtered and reduced to an oil by rotary evaporation. This was purified by flash chromatography, eluting with n-hexane and ethyl acetate. Appropriate fractions were collected for the product peak and were reduced by rotary evaporation to obtain a clear oil (2.1 g, 93%). The structure was confirmed as methyl 3-methylsulfonyl-oxy-benzoate by 1H NMR.

To a reactor was charged methyl 3-methylsulfonyl-oxybenzoate (0.54 g) and methanol (4.6 ml), and this was stirred until dissolved. 10% palladium on charcoal (56 mg) and diethylamine (230 mg, 325.3 µL) were then charged. The reactor was sealed and then the atmosphere was flushed with hydrogen gas. The reaction was stirred at ambient temperature for 16 hours under a positive pressure of hydrogen gas. After removal of the hydrogen atmosphere, the mixture was filtered through a 0.45 µm filter. Dichloromethane (20 ml) and water (10 ml) were then charged to the methanolic solution, and the mixture vigorously mixed. The organic phase was separated and the aqueous phase was extracted with dichloromethane (2×10 ml). The combined organic phase was dried (MgSO$_4$), filtered and reduced to an oil by rotary evaporation. This was purified by flash chromatography, eluting with n-hexane and ethyl acetate. Appropriate fractions were collected for the product peak and were reduced by rotary evaporation to obtain a clear liquid (281 mg, 88%). The structure was confirmed as methyl benzoate by 1H NMR.

EXAMPLE 28 Synthesis of Benzoic Acid

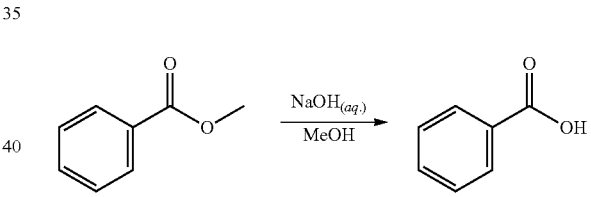

A reactor was charged with methyl benzoate (136 mg) and a 1.25M solution of sodium hydroxide (200 mg) in water (4 ml). The reactor was sealed and the mixture stirred at ambient temperature for 1 hour. The solution was then acidified to pH 1 with concentrated hydrochloric acid. This caused a precipitate to form, and this was isolated by filtration, and washed with a 10% aqueous solution of hydrochloric acid (5 ml). The resulting solid was dried for 16 hours (50° C., 150 mBar) to yield a white solid (68 mg, 56%). The structure was confirmed as benzoic acid by 1H NMR.

EXAMPLE 29 Synthesis of 2-aminophenol

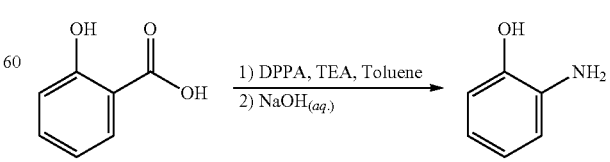

A reactor was charged with 2-hydroxybenzoic acid (665 mg), diphenylphosphoryl azide (1.28 g, 1 ml), triethylamine (479 mg, 0.66 ml) and toluene (10 ml). The reactor was sealed, heated to 110° C. and held for 16 hours. After cooling to ambient temperature, the mixture was quenched with water (20 ml) and then the organics were separated. The aqueous phase was extracted with ethyl acetate (3×20 ml), and the combined organic phase was then washed saturated aqueous sodium chloride solution (10 ml). The combined organic phase was dried (MgSO$_4$), filtered and reduced to an oil by rotary evaporation. This was purified by flash chromatography, eluting with n-hexane and ethyl acetate. Appropriate fractions were collected for the product peak and were reduced by rotary evaporation to obtain 1,3-benzoxazol-2 (3H)-one as a yellow liquid (309 mg, 48%).

A reactor was charged with 1,3-benzoxazol-2(3H)-one (309 mg) and a 2.5M solution of sodium hydroxide (1.5 g) in water (15 ml). The reactor heated to 100° C. and held for 16 hours. The reaction mixture was cooled to ambient temperature then acidified to pH 1 with concentrated hydrochloric acid. The organics were then extracted with ethyl acetate (20 ml). The aqueous phase was basified with 10% aqueous sodium bicarbonate solution to pH 9 and then the organics were extracted with ethyl acetate (3×20 ml). The combined organic phase was dried (MgSO$_4$), filtered and reduced to an oil by rotary evaporation. This was purified by flash chromatography, eluting with n-hexane and ethyl acetate. Appropriate fractions were collected for the product peak and were reduced by rotary evaporation to obtain the desired product as orange oil (180 mg, 72%). The structure was confirmed as 2-aminophenol by 1H NMR.

EXAMPLE 30 Synthesis of Phenol

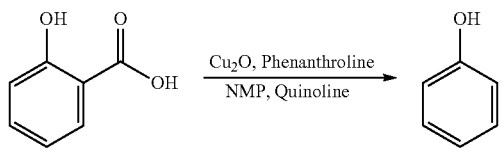 [SMILES: O=C(O)c1ccccc1O ; "Cu2O, Phenanthroline" ; "NMP, Quinoline" ; Oc1ccccc1]

A reactor was charged with 2-hydroxybenzoic acid (91 mg), copper(I) oxide (10 mg), 1,10-phenanthroline (24 mg), NMP (1 ml) and quinoline (364 mg, 333 µL). The reactor was sealed, heated to 165° C., and held for 40 hours, with stirring. The reaction mixture was cooled to ambient temperature then brought directly onto silica and purified by flash chromatography, eluting with n-hexane and ethyl acetate. Appropriate fractions were collected for the product peak and were reduced by rotary evaporation to yield a yellow liquid. This was dissolved in dichloromethane (10 ml) and washed with 1N aqueous hydrochloric acid solution (2×10 ml) and subsequently with water (10 ml). The combined aqueous phase was extracted with dichloromethane (3×5 ml). All the organic phases were combined and dried (MgSO$_4$), filtered, and reduced by rotary evaporation to obtain the desired product as orange oil (21 mg, 33%). The structure was confirmed as phenol by 1H NMR.

EXAMPLE 31 Synthesis of Phenol

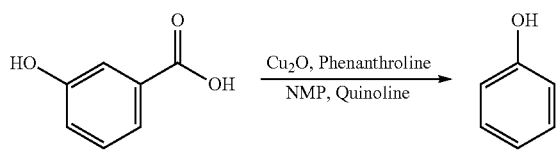 [SMILES: O=C(O)c1cccc(O)c1 ; "Cu2O, Phenanthroline" ; "NMP, Quinoline" ; Oc1ccccc1]

A reactor was charged with 3-hydroxybenzoic acid (91 mg), copper(I) oxide (10 mg), 1,10-phenanthroline (24 mg), NMP (1 ml) and quinoline (364 mg, 333 µL). The reactor was sealed, heated to 165° C., and held for 40 hours, with stirring. The reaction mixture was cooled to ambient temperature then brought directly onto silica and purified by flash chromatography, eluting with n-hexane and ethyl acetate. Appropriate fractions were collected for the product peak and were reduced by rotary evaporation to yield a yellow liquid. This was dissolved in dichloromethane (10 ml) and washed with 1N aqueous hydrochloric acid solution (2×10 ml) and subsequently with water (10 ml). The combined aqueous phase was extracted with dichloromethane (3×5 ml). All the organic phases were combined and dried (MgSO$_4$), filtered, and reduced by rotary evaporation to obtain the desired product as orange oil (65 mg, 50%). The structure was confirmed as phenol by 1H NMR.

EXAMPLE 32 Synthesis of 4-methylphenol

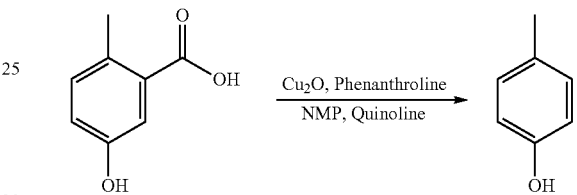

A reactor was charged with 5-hydroxy-2-methylbenzoic acid (100 mg), copper(I) oxide (10 mg), 1,10-phenanthroline (24 mg), NMP (1 ml) and quinoline (364 mg, 333 µL). The reactor was sealed, heated to 170° C., and held for 40 hours, with stirring. The reaction mixture was cooled to ambient temperature then brought directly onto silica and purified on a Reveleris® X2 Flash Chromatography System, eluting with n-hexane and ethyl acetate. Appropriate fractions were collected for the product peak and were reduced by rotary evaporation to yield a yellow liquid. This was dissolved in dichloromethane (10 ml) and washed with 1N aqueous hydrochloric acid solution (2×10 ml) and subsequently with water (10 ml). The combined aqueous phase was extracted with dichloromethane (3×5 ml). All the organic phases were combined and dried (Na$_2$SO$_4$), filtered, and reduced by rotary evaporation to obtain the desired product as orange oil (33 mg, 47%). The structure was confirmed as 4-methylphenol by 1H NMR.

EXAMPLE 33 Synthesis of 4-hydroxybenzoic Acid

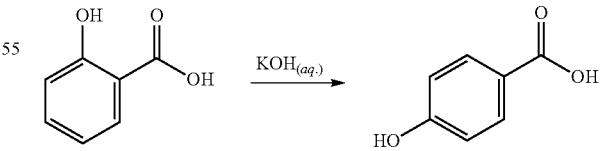

To a reactor was charged 2-hydroxybenzoic acid (3.5 g), 16N aqueous potassium hydroxide solution (3.25 ml) and water (1.5 ml). The solution was then concentrated by distillation until a white slightly wet solid remained. This solid, potassium 2-hydroxybenzoate, was dried in a vacuum oven (190° C., 2 mBar, 3 hours) to yield a dry white solid. Then reactor was then heated to 240° C. and held for 3 hours. The reaction mixture was cooled to ambient temperature then water was added (4 ml). The mixture was then acidified to pH 1 with concentrated hydrochloric acid, and this caused a precipitate to form. This was isolated by filtration and washed with water (5 ml), before being dried in a vacuum oven (50° C., 100 mbar, 16 hours). This yielded the desired product as a white solid (2.1 g, 61%). The structure was confirmed as 4-methylbenzoic acid by 1H NMR.

EXAMPLE 34 Synthesis of 2-acetoxybenzoic Acid

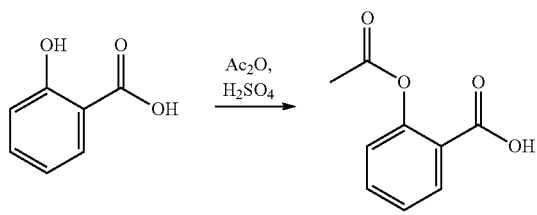

To a reactor was charged 2-hydroxybenzoic acid (1.0 g) and acetic anhydride (1.53 g, 1.42 ml). To this was added a catalytic amount of concentrated sulphuric acid (5 drops). The reactor was sealed and heated to 50° C. and held for 20 minutes. The reaction mixture was cooled to ambient temperature then ice-cold water was added (15 ml) with vigorous mixing, causing a precipitate to form. This was isolated by filtration and washed with ice-cold water (3×5 ml), before being dried in a vacuum oven (50° C., 150 mbar, 3 hours). This yielded the desired product as a white solid (941 mg, 70%). The structure was confirmed as 2-acetoxybenzoic acid by 1H NMR.

EXAMPLE 35 Synthesis of 2-hydroxybenzyl Alcohol

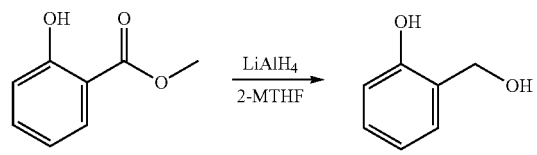

To a reactor was charged lithium aluminium hydride (1.247 g) and 2-methyltetrahydrofuran (8 ml). The stirring was started and the suspension was cooled to −15° C. A solution of methyl 2-hydroxybenzoate (500 mg) in 2-methyltetrahydrofuran (2 ml) was added drop-wise over 10 minutes. The reaction was allowed to warm to room temperature and stir for 24 hours. The reaction mixture was cooled to −15° C. then was carefully added dropwise over 15 minutes to a second reactor which was filled with stirred ice (~50 ml). Conc. sulfuric acid was then added until all of the aluminium salts were dissolved. The organics were extracted with 2-methyltetrahydrofuran (2×10 ml), and the combined organics were washed with water (10 ml), dried ($Na_2SO_4$) and filtered. The organic solution was reduced by rotary evaporation to yield an oil, which was purified on a Reveleris® X2 Flash Chromatography System, eluting with n-hexane and ethyl acetate. Appropriate fractions were collected for the product peak and were reduced by rotary evaporation to obtain the desired product as a clear oil (381 mg, 93%). The structure was confirmed as 2-hydroxybenzyl alcohol by 1H NMR.

EXAMPLE 36 Synthesis of 3-hydroxybenzyl Alcohol

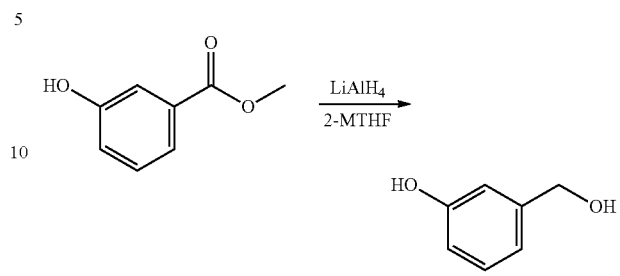

To a reactor was charged lithium aluminium hydride (1.247 g) and 2-methyltetrahydrofuran (8 ml). The stirring was started and the suspension was cooled to −15° C. A solution of methyl 3-hydroxybenzoate (500 mg) in 2-methyltetrahydrofuran (2 ml) was added drop-wise over 10 minutes. The reaction was allowed to warm to room temperature and stir for 24 hours. The reaction mixture was cooled to −15° C. then was carefully added dropwise over 15 minutes to a second reactor which was filled with stirred ice (~50 ml). Conc. sulfuric acid was then added until all of the aluminium salts were dissolved. The organics were extracted with 2-methyltetrahydrofuran (2×10 ml), and the combined organics were washed with water (10 ml), dried ($Na_2SO_4$) and filtered. The organic solution was reduced by rotary evaporation to yield an oil, which was purified on a Reveleris® X2 Flash Chromatography System, eluting with n-hexane and ethyl acetate. Appropriate fractions were collected for the product peak and were reduced by rotary evaporation to obtain the desired product as a colourless oil (350 mg, 86%). The structure was confirmed as 3-hydroxybenzyl alcohol by 1H NMR.

EXAMPLE 37 Synthesis of 2-hydroxystyrene

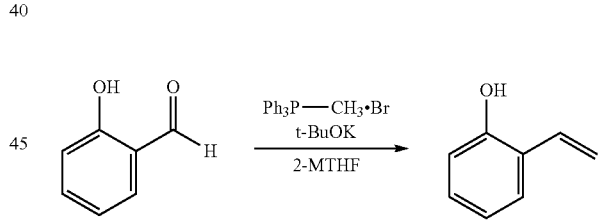

A reactor was charged potassium tert-butoxide (773 mg) and 2-methyltetrahydrofuran (6.9 ml) and this was stirred. To a separate reactor was charged methyltriphenylphosphonium bromide (2.464 g) and 2-methyltetrahydrofuran (6.9 ml), and this was stirred for 5 minutes. To this, the potassium tert-butoxide solution was added dropwise over 15 minutes, and this was stirred at room temperature for 3 hours. The reaction mixture was then cooled to around −20° C. and a solution of 2-hydroxybenzaldehyde (366 mg) in 2-methyltetrahydrofuran (2 ml) was added over 1 hour. The reaction was allowed to warm slowly to room temperature and stir for 24 hours. At this point, the reaction mixture was still yellow, but was browner than the day before (See Photo 2). The reaction was quenched by the careful addition of 1M aqueous hydrochloric acid (15 ml), and the organics were separated. The aqueous was extracted with 2-methyltetrahydrofuran (10 ml), and the combined organics were washed with saturated aqueous sodium bicarbonate solution (10 ml), then water (10 ml), and dried (Na$_2$SO$_4$) and filtered. The organic solution was reduced by rotary evaporation to yield an oil, which was purified on a Reveleris® X2 Flash Chromatography System, eluting with n-hexane and ethyl acetate. Appropriate fractions were collected for the product peak and were reduced by rotary evaporation to obtain the desired product as a colourless oil (295 mg, 82%). The structure was confirmed as 2-hydroxystyrene alcohol by 1H NMR.

EXAMPLE 38 Synthesis of 3-hydroxystyrene

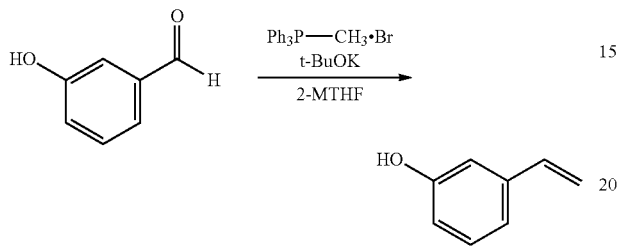

A reactor was charged potassium tert-butoxide (773 mg) and 2-methyltetrahydrofuran (6.9 ml) and this was stirred. To a separate reactor was charged methyltriphenylphosphonium bromide (2.464 g) and 2-methyltetrahydrofuran (6.9 ml), and this was stirred for 5 minutes. To this, the potassium tert-butoxide solution was added dropwise over 15 minutes, and this was stirred at room temperature for 3 hours. The reaction mixture was then cooled to around −20° C. and a solution of 3-hydroxybenzaldehyde (366 mg) in 2-methyltetrahydrofuran (2 ml) was added over 1 hour. The reaction was allowed to warm slowly to room temperature and stir for 24 hours. At this point, the reaction mixture was still yellow, but was browner than the day before (See Photo 2). The reaction was quenched by the careful addition of 1M aqueous hydrochloric acid (15 ml), and the organics were separated. The aqueous was extracted with 2-methyltetrahydrofuran (10 ml), and the combined organics were washed with saturated aqueous sodium bicarbonate solution (10 ml), then water (10 ml), and dried (Na$_2$SO$_4$) and filtered. The organic solution was reduced by rotary evaporation to yield an oil, which was purified on a Reveleris® X2 Flash Chromatography System, eluting with n-hexane and ethyl acetate. Appropriate fractions were collected for the product peak and were reduced by rotary evaporation to obtain the desired product as a colourless oil (295 mg, 82%). The structure was confirmed as 3-hydroxystyrene alcohol by 1H NMR.

EXAMPLE 39 Synthesis of 3-hydroxybenzoic Acid

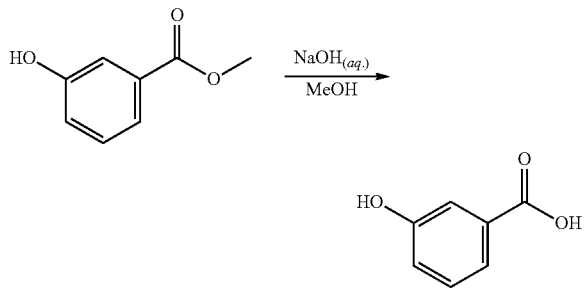

A reactor was charged with methyl 3-hydroxybenzoate (500 mg) and then methanol (15 ml) was added, and this mixture was stirred until the solid was dissolved. Sodium hydroxide (394 mg) was dissolved in water (5 ml), and this solution was added to the methanol solution and the reaction mixture was heated to 80° C. and held for 4 hours. The reaction mixture was washed with dichloromethane (2×10 ml). The aqueous layer was acidified to pH~2 with 1M aqueous hydrochloric acid solution and then the organics were extracted twice with dichloromethane (2×10 ml). The combined organics were dried (Na$_2$SO$_4$), filtered and reduced to yield an oil, which was purified on a Reveleris® X2 Flash Chromatography System, eluting with n-hexane and ethyl acetate. Appropriate fractions were collected for the product peak and were reduced by rotary evaporation to obtain the desired product as a colourless oil (285 mg, 63%). The structure was confirmed as 3-hydroxybenzoic acid by 1H NMR.

EXAMPLE 40 Synthesis of 3-hydroxybenzyl Bromide

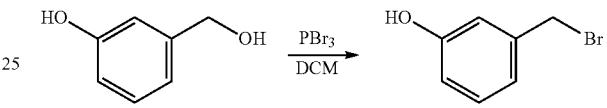

A reactor was charged with 3-hydroxybenzyl alcohol (500 mg), and dichloromethane (5 ml) and the mixture cooled to −15° C. Phosphorous tribromide (568 µL) was added dropwise and the reaction was allowed to warm to room temperature over 3 hours. The reaction was quenched by the dropwise addition of water (10 ml) and the organics were separated. The aqueous was washed with dichloromethane (2×10 ml) and the combined organics were washed with saturated aqueous sodium bicarbonate solution (10 ml), then water (10 ml). The organics were dried (Na$_2$SO$_4$), filtered and reduced to yield an oil, which was purified on a Reveleris® X2 Flash Chromatography System, eluting with n-hexane and ethyl acetate. Appropriate fractions were collected for the product peak and were reduced by rotary evaporation to obtain the desired product as a white solid (446 mg, 59%). The structure was confirmed as 3-hydroxybenzyl bromide by 1H NMR.

EXAMPLE 41 Synthesis of 3-methylphenol

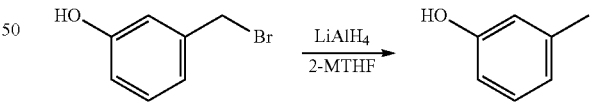

To a reactor was charged lithium aluminium hydride (905 g) and 2-methyltetrahydrofuran (8 ml). The stirring was started and the suspension was cooled to −15° C. A solution of methyl 3-hydroxybenzyl bromide (446 mg) in 2-methyltetrahydrofuran (2 ml) was added drop-wise over 10 minutes. The reaction was allowed to warm to room temperature and stir for 24 hours. The reaction mixture was cooled to −15° C. then was carefully added dropwise over 15 minutes to a second reactor which was filled with stirred ice (~50 ml). Conc. sulfuric acid was then added until all of the aluminium salts were dissolved. The organics were extracted with 2-methyltetrahydrofuran (2×10 ml), and the combined organics were washed with water (10 ml), dried (Na$_2$SO$_4$) and filtered. The organic solution was reduced by rotary evaporation to yield an oil, which was purified on a Reveleris® X2 Flash Chromatography System, eluting with n-hexane and ethyl acetate. Appropriate fractions were collected for the product peak and were reduced by rotary evaporation to obtain the desired product as a colourless oil (229 mg, 89%). The structure was confirmed as 3-methylphenol by 1H NMR.

The invention claimed is:

1. A method for preparing a final phenolic product from biomass comprising the steps of:
   a) providing a furanic compound obtainable from C4-, C5-, or C6-sugar units from biomass;
   b) reacting the furanic compound with a dienophile to obtain a phenolic compound; and
   c) reacting the phenolic compound further in a hydrolysis reaction followed by an oxidation reaction, or in a hydrolysis reaction followed by a decarboxylation reaction, or in a hydrolysis reaction followed by a rearrangement reaction, or in a reduction reaction, or in a nucleophilic substitution to obtain the final phenolic product.

2. Method according to claim 1, wherein the phenolic compound is obtained by ring-opening of a bicyclic adduct that is obtained by reacting the furanic compound with the dienophile.

3. Method according to claim 1, wherein the furanic compound is a compound according to formula I

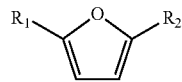

wherein $R_1$ and $R_2$ are independently selected from the group consisting of H, linear or branched $C_1$-$C_8$-alkyl, F, Cl, Br, I, —$CH_2F$, —$CH_2Cl$, —$CH_2Br$, —$CH_2I$, —CN, —$NO_2$, —COH, —$CO_2H$ and esters thereof, —$CH_2NH_2$ and secondary, tertiary and quaternary amines or amides thereof and —$CH_2OH$ and esters or ethers thereof, optionally bound to a solid support.

4. Method according to claim 1, wherein the dienophile is a compound according to formula (II)

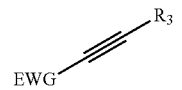

wherein EWG is an electron withdrawing group; and wherein $R_3$ is H, linear or branched $C_1$-$C_8$-alkyl, or an EWG.

5. Method according to claim 1, wherein the step of reacting the furanic compound with the dienophile is catalyzed by a catalyst which is a protic or Lewis acid, optionally supported on a polymer or a heterogeneous support such as silica.

6. Method according to claim 1, wherein the furanic compound is reacted with the dienophile at a temperature of −60-350° C.

7. Method according to claim 1, wherein the furanic compound is reacted with the dienophile at a pressure of 0-200 bar.

8. Method according to claim 1, wherein reacting the phenolic compound is performed in one or more suitable solvents.

9. Method according to claim 2, wherein the bicyclic adduct, before ring-opening, is reacted in one or more reaction steps selected from the group consisting of hydrolysis, oxidation, reduction, nucleophilic addition, olefination, nitrosation, elimination, condensation, electrophilic substitution, rearrangement, decarboxylation, decarbonylation and combinations thereof.

10. Method according to claim 1, wherein the final phenolic product is one or more phenolic selected from the group consisting of compounds according to the following formulae:

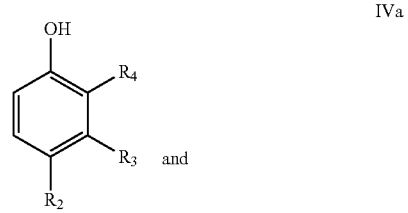

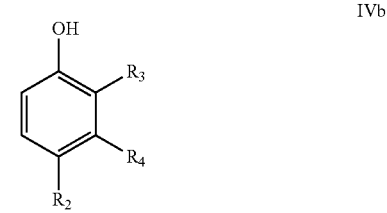

wherein
   $R_2$=—H, linear or branched $C_1$-$C_8$-alkyl, —CH=$CH_2$, —$CO_2X$, —C(O)$NX_2$, —$CH_2OX$, —$CH_2NX_2$, —CHO, —OX, —CN, —$NO_2$, —C(O)NX, —C(=NY)X, —$CF_3$, —$CCl_3$, —$CBr_3$, —$CI_3$, —$SO_2X$, —$SO_3X$, —$NX_2$, —COX, —COF, —COCl, —COBr, or —COI; and/or
   $R_3$=—H, linear or branched $C_1$-$C_8$-alkyl, —CH=$CH_2$, —$CO_2X$, —C(O)$NX_2$, —$CH_2OX$, —$CH_2NX_2$, —CHO, —OX, —CN, —$NO_2$, —C(O)NX, —C(=NY)X, —$CF_3$, —$CCl_3$, —$CBr_3$, —$CI_3$, —$SO_2X$, —$SO_3X$, —$NX_2$, —COX, —COF, —COCl, —COBr, or —COI; and
   $R_4$=—H, linear or branched $C_1$-$C_8$-alkyl, —CH=$CH_2$, —$CO_2X$, —C(O)$NX_2$, —$CH_2OX$, —$CH_2NX_2$, —CHO, —OX, —CN, —$NO_2$, —C(O)NX, —C(=NY)X, —$CF_3$, —$CCl_3$, —$CBr_3$, —$CI_3$, —$SO_2X$, —$SO_3X$, —$NX_2$, —COX, —COF, —COCl, —COBr, or —COI, wherein X and Y are independently H, or linear or branched $C_1$-$C_8$-alkyl, optionally substituted with halogens and optionally polymer-supported.

11. Method according to claim 1, wherein the final phenolic product is one or more phenolic selected from the group consisting of compounds according to the following formulae:

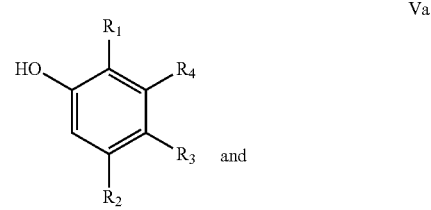

-continued

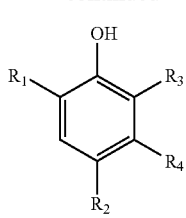

Vb wherein
R$_1$=linear or branched C$_1$-C$_8$-alkyl, —CH═CH$_2$, —CO$_2$X, —C(O)NX$_2$, —CH$_2$OX, —CH$_2$NX$_2$, —CHO, —OX, —CN, —NO$_2$, —C(O)NX, —C(═NY)X, —CF$_3$, —CCl$_3$, —CBr$_3$, —Cl$_3$, —SO$_2$X, —SO$_3$X, —NX$_2$, —COX, —COF, —COCl, —COBr, or —COI, wherein X and Y are independently H, or linear or branched C$_1$-C$_8$-alkyl, optionally substituted with halogens and optionally polymer-supported; and R$_2$=—H, linear or branched C$_1$-C$_8$-alkyl, —CH═CH$_2$, —CO$_2$X, —C(O)NX$_2$, —CH$_2$OX, —CH$_2$NX$_2$, —CHO, —OX, —CN, —NO$_2$, —C(O)NX, —C(═NY)X, —CF$_3$, —CCl$_3$, —CBr$_3$, —Cl$_3$, —SO$_2$X, —SO$_3$X, —NX$_2$, —COX, —COF, —COCl, —COBr, or —COI, wherein X and Y are independently H, or linear or branched C$_1$-C$_8$-alkyl, optionally substituted with halogens and optionally polymer-supported; and R$_3$=—H, linear or branched C$_1$-C$_8$-alkyl, —CH═CH$_2$, —CO$_2$X, —C(O)NX$_2$, —CH$_2$OX, —CH$_2$NX$_2$, —CHO, —OX, —CN, —NO$_2$, —C(O)NX, —C(═NY)X, —CF$_3$, —CCl$_3$, —CBr$_3$, —Cl$_3$, —SO$_2$X, —SO$_3$X, —NX$_2$, —COX, —COF, —COCl, —COBr, or —COI, wherein X and Y are independently H, or linear or branched C$_1$-C$_8$-alkyl, optionally substituted with halogens and optionally polymer-supported; and R$_4$=—H, linear or branched C$_1$-C$_8$-alkyl, —CH═CH$_2$, —CO$_2$X, —C(O)NX$_2$, —CH$_2$OX, —CH$_2$NX$_2$, —CHO, —OX, —CN, —NO$_2$, —C(O)NX, —C(═NY)X, —CF$_3$, —CCl$_3$, —CBr$_3$, —Cl$_3$, —SO$_2$X, —SO$_3$X, —NX$_2$, —COX, —COF, —COCl, —COBr, or —COI, wherein X and Y are independently H, or linear or branched C$_1$-C$_8$-alkyl, optionally substituted with halogens and optionally polymer-supported.

12. Method according to claim 1, wherein the final phenolic product is one or more phenolic selected from the group consisting of phenol, o-alkylphenol, m-alkylphenol, p-alkylphenol, cresol, o-hydroxybenzoic acid, m-hydroxybenzoic acid, p-hydroxybenzoic acid, 2,6-dialkylphenol, 2,5-dialkylphenol, 2,4-dialkylphenol, 2,3-dialkylphenol, 3,4-dialkylphenol, 3,5-dialkylphenol, xylenols, 2,3,4-trialkylphenol, 2,3,5-trialkylphenol, 2,3,6-trialkylphenol, 2,4,5-trialkylphenol, 2,4,6-trialkylphenol, 3,4,5-trialkylphenol, o-nitrophenol, m-nitrophenol, p-nitrophenol, o-cyanophenol, m-cyanophenol, p-cyanophenol, catechol, resorcinol, hydroquione, o-halophenol, m-halophenol, p-halophenol, o-aminophenol, m-aminophenol, p-aminophenol, o-hydroxystyrene, m-hydroxystyrene, p-hydroxystyrene, o-hydroxybenzyl alcohol, m-hydroxybenzyl alcohol, p-hydroxybenzyl alcohol, o-hydroxybenzyl amine, m-hydroxybenzyl amine, p-hydroxybenzyl amine, o-hydroxyacetophenone, m-hydroxyacetophenone, p-hydroxyacetophenone, o-hydroxybenzaldehyde, m-hydroxybenzaldehyde, p-hydroxybenzaldehyde, o-hydroxybenzamide, m-hydroxybenzamide and p-hydroxybenzamide.

13. A method for preparing a final phenolic product from biomass comprising the steps of:
a) providing a furanic compound obtainable from biomass, wherein the furanic compound is furan;
b) reacting the furanic compound with a dienophile to obtain a phenolic compound; and
c) reacting the phenolic compound further to obtain the final phenolic product.

14. Method according to claim 4, wherein EWG=—CN, —NO$_2$, —CO$_2$X, —C(O)NX, —C(═NY)X, CF$_3$, CCl$_3$, CBr$_3$, Cl$_3$, —SO$_2$X, —SO$_3$X, —COH, —COX, —COF, —COCl, —COBr, —COI, and wherein X and Y are independently H, or linear or branched C$_1$-C$_8$-alkyl, optionally substituted with halogens and optionally polymer-supported.

15. Method according to claim 6, wherein the furanic compound is reacted with the dienophile at a temperature of −20-250° C.

16. Method according to claim 6, wherein the furanic compound is reacted with the dienophile at a temperature of 20-150° C.

17. Method according to claim 7, wherein the furanic compound is reacted with the dienophile at a pressure of 1-50 bar.

18. Method according to claim 8, wherein reacting the phenolic compound is performed in one or more suitable solvents in a concentration of 0.1-3 M.

19. Method according to claim 8, wherein reacting the phenolic compound is performed in one or more suitable solvents in a concentration of about 2 M.

20. Method according to claim 8, wherein said one or more solvents are selected from the group consisting of water, alcohols, esters, ketones, aliphatic hydrocarbons, aromatic hydrocarbons, organic acids, ethers, diprotic apolar solvents, halogenated solvents, nitrated solvents, ionic liquids, organic bases and combinations thereof.

* * * * *